United States Patent [19]

Gall

[11] 4,338,453
[45] Jul. 6, 1982

[54] AMINOALKYL-1,2,4-TRIAZOLES

[75] Inventor: Martin Gall, Kalamazoo, Mich.

[73] Assignee: The Upjohn Company, Kalamazoo, Mich.

[21] Appl. No.: 187,920

[22] Filed: Sep. 17, 1980

[51] Int. Cl.$^3$ .................. C07D 249/08; C07D 241/06; C07D 233/10; C07D 295/02
[52] U.S. Cl. .................................... 548/263; 548/262; 548/333; 548/336; 546/193; 546/210; 544/366
[58] Field of Search ................ 546/193, 210; 548/262, 548/263

[56] References Cited

U.S. PATENT DOCUMENTS

| | | | |
|---|---|---|---|
| 3,505,350 | 4/1970 | Doebel et al. | 548/336 |
| 3,651,080 | 3/1972 | Doebel et al. | 548/336 |
| 3,882,134 | 5/1975 | Baldwin et al. | 546/193 |
| 3,910,943 | 10/1975 | Gall et al. | 548/262 |
| 4,102,889 | 7/1978 | Baldwin et al. | 546/193 |
| 4,111,944 | 9/1978 | Novello et al. | 546/193 |
| 4,115,572 | 9/1978 | Paul et al. | 548/336 |
| 4,207,324 | 6/1980 | Matsumura et al. | 548/335 |

FOREIGN PATENT DOCUMENTS

| | | | |
|---|---|---|---|
| 810117 | 5/1974 | Belgium . | |
| 856356 | 1/1978 | Belgium . | |
| 875846 | 10/1979 | Belgium . | |
| 2524119 | 12/1975 | Fed. Rep. of Germany | 548/262 |
| 2132632 | 2/1972 | France | 548/336 |
| 54-109974 | 8/1979 | Japan . | |
| 1134580 | 10/1967 | United Kingdom . | |
| 2016011 | 3/1979 | United Kingdom | 548/336 |

OTHER PUBLICATIONS

Agents and Actions, 9:235-238, (1979) H. G. Johnson, et al.
Journal of Medicinal Chemistry, 21, No. 6, 542-548, (1978), Martin Gall et al.
Merck Manual 12th ed. 465-471 (1972).
Goodman and Gillman: The Pharmacological Basis of Therapeutics, 4th ed., 728-744 (1970).
Antwoulers, F., et al., Experientia 33:1657 (1977).
Gonsior, E., et al., Intern. J. Clin. Pharmacol. and Biopharm. 17:283 (1979).

Primary Examiner—Anton H. Sutto
Assistant Examiner—Sharon A. Gibson
Attorney, Agent, or Firm—Lawrence T. Welch

[57] ABSTRACT

Novel aminoalkyl triazoles are provided which are useful for the treatment of sensitized humans and animals for allergies and anaphylactic reactions. Additionally, a number of the compounds are useful in the treatment of hypertension. These compounds are of the formula

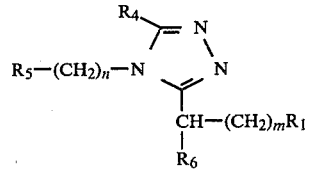

wherein $R_4$ is hydrogen, alkyl, alkoxy, aryl, sulfonyl, or sulfinyl, $R_5$ is aryl, $R_6$ is hydrogen, hydroxy, alkyl, alkoxy, or alkanoyloxy, and $R_1$ is piperidinyl or amino.

16 Claims, No Drawings

AMINOALKYL-1,2,4-TRIAZOLES

DESCRIPTION

BACKGROUND OF THE INVENTION

The present invention provides novel organic compounds. In particular, this invention relates to substituted imidazoles and substituted 1,2,4-triazoles.

The present invention also relates to novel methods for the synthesis and use of the novel organic compounds disclosed herein. The specification particularly relates to novel organic compounds for use as antiallergy agents, whereby they prevent the symptoms manifest in such states as asthma, seasonal pollinosis, allergic rhinitis, urticaria, allergic conjunctivitis, food allergy, and anaphylactoid reactions of a sensitized animal, especially man. Some of the novel compounds herein described also exhibit antihypertensive activity as well as antiallergy activity, and as such are useful in the treatment of hypertension.

Allergy is a condition whose chief manifestation is an allergic hypersensitivity reaction (AHR). AHR's are broad in their symptomology. The symptoms may include dermatitis, lacrimation, nasal discharge, cough, sneezing, nausea, vomiting, diarrhea, difficulty in breathing, pain, inflammation, and, in severe cases, anaphylactic shock, circulatory collapse, and even death. This manifestation is found in animals suffering from bronchial asthma, seasonal pollinosis (e.g., hayfever), allergic rhinitis, urticaria, allergic conjunctivitis, food allergies, and anaphylactoid reactions. The substances most frequently responsible for the clinical manifestations of AHR are plant pollen, animal feathers and danders, dust, milk, and wheat, whether inhaled or ingested.

AHR's are found in man as well as other animals. In an AHR an antibody (reagin in man) influences the cell membrane of a mast cell by reacting with an antigen, to initiate reactions within the mast cell which ultimately causes release of mediator (bioactive amine) such as bradykinin, slow reacting substance A (SRS-A), histamine, serotonin (5HT), possibly some prostaglandins, and possibly other unknown substances. The mediator is released from the mast cell where it attaches to suitable receptor sites (e.g., on smooth muscle) resulting in AHR attack symptoms. Various methods are used to relieve the symptoms of AHR including (1) avoiding attack by the antigen, (2) blocking production of antibody with an immunosuppresant, (3) blocking the receptor sites of the mediator, e.g., antihistamine, (4) using of bronchodilators, and (5) blocking reaction of antibody with the mast cell.

Hypertension is a condition which is often characterized by the arterioles exhibiting abnormal resistance to the flow of blood and is usually associated with an abnormal increase in systolic, diastolic, and mean arterial blood pressures. Arterial pressure is the product of cardiac output times the total peripheral resistance. An increase in either of these two factors therefore can cause hypertension. However, in most types of hypertension one finds the total peripheral resistance is greatly increased while the cardiac output is near to normal. Disease states exhibiting hypertension include renal hypertension, Goldblatt's hypertension, tumor-induced hypertension, and essential hypertension where etiology is unknown. Elevation of blood pressure has been induced in animals through the central nervous system, by neurogenic, renal and adrenal mechanisms, by ingestion of large amounts of sodium chloride, as well as by administration of certain drugs. Although all these mechanisms may play a part, heredity is a predisposing factor, suggesting a genetic contribution of some kind. Irrespective of the etiology of the condition, the elevated pressure per se accelerates a number of degenerative processes that shorten life expectancy. See Goodman and Gillman: The Pharmacological Basis of Therapeutics, 4th ed., 728–744 (1970).

Treatment of hypertension may be by treatment of the etiology of the hypertension or by the introduction of drugs that exhibit a direct effect on blood pressure. A patient who would be considered for treatment with pharmacologic agents is readily diagnosed by an attending physician. Indications for pharmacologic treatment include conditions where the patient has malignant hypertension, where the diastolic pressure is persistently above 95 mm Hg or where there is vascular disease related to the hypertensive state. These states may be readily determined by an attending physician of ordinary skill, See the Merck Manual 12th ed. 465–471 (1972).

Various imidazoles and 1,2,4-triazoles are well known in the prior art. These compounds have been described as useful for a wide range of uses. Such known imidazole compounds include 1,2,4,5-tetrasubstituted imidazoles useful as hypotensive, antitumor, antiviral, antiinflammatory agents, and as protective agents against, cerebral anoxia or hypoxia such as are described in British Pat. No. 2,016,011 (abstracted in Derwent Farmdoc CPI no. 68606B/38). French Pat. No. 2,132,632 (abstracted in Derwent Farmdoc CPI No. 10105U-B), U.S. Pat. No. 3,651,080, and Belgian Patent 810,117 (abstracted in Farmdoc CPI No. 41717V/23); 1-substituted imidazoles for use in treating inflammation, hypertension, thrombosis and asthma such as described in Japanese Patent Application 109974 (abstracted in Derwent Farmdoc CPI No. 72897B/40); 1,2-di-substituted-4-haloimidazoles-5-acetic acid derivatives for use as diuretics and hypotensives, as described in U.S. Pat. No. 4,207,324; and 1,4,5-trisubstituted imidazoles useful as antiallergic and hypotensive agent such as described in British Pat. No. 1,134,580. Known 1,2,4-triazole compounds include 1,3,5-trisubstituted 1,2,4-triazoles useful as: antiasthma and antiallergic agents as described in Netherlands Patent Application 06067 (abstracted in Derwent Farmdoc CPI No. 86573V/50); antihyperuricacidemic, diuretic, and hypotensive agents as described in U.S. Pat. No. 4,102,889 and U.S. Pat. No. 4,111,944; and as antiinflammatory agents as described in Belgian Pat. No. 875846 (abstracted in Derwent Farmdoc CPI No. 77110B/44). 3-substituted triazoles useful as hypotensives are also known such as described in Belgian Pat. No. 856356 (abstracted in Derwent Farmdoc CPI No. 02073A/02).

PRIOR ART

Pharmacologically active imidazoles and triazoles are known as indicated above. Some compounds are known to inhibit both the release and effects of AHR mediators. Oxatomide, a benzimidazole, is one compound which shows such an effect. (See Antwoulers, F., et al., Experientia 33:1657 (1977)). Anti-allergic effects have also been disclosed for a coumarin compound: (1-(4-chlorobenzyl)-4-[3-(3,4-dimethylcoumarin-7-yl-oxy)-propyl]-piperazine, dihydrochloride, see Gonsior, E., et

SUMMARY OF THE INVENTION

The present invention particularly provides a compound according to Formula I, or a pharmacologically acceptable salt thereof,
wherein $X_1$ is:
- (a) =CH—;
- (b) =(CH$_3$)—; or
- (c) =N—;

wherein m is zero, one, 2 or 3;
wherein n is zero, one or 2,
wherein $R_1$ is:
- (a) 1-piperidinyl substituted at the 3 or 4 position by $R_5$, whereby $R_5$ is defind as below;
- (b) —N(CH$_3$)—(CH$_2$)$_p$—$R_{15}$, wherein $R_{15}$ is defined as below and wherein p is 1, 2, or 3;
- (c) —NH—(CH$_2$)$_p$—$R_{15}$, wherein p and $R_{15}$ are as defined below; or
- (d) a piperazinyl group of Formula II, wherein $R_7$ and $R_8$ are as defined below;

wherein $R_4$ is:
- (a) hydrogen;
- (b) alkyl of one to three carbon atoms, inclusive;
- (c) $R_{54}OCH_2$—, wherein $R_{54}$ is defined below;
- (d) —CH($R_{35}$)(OH);
- (e) —$R_{35}$;
- (f) —SH; or
- (g) S(O)$_1R_{17}$, wherein q is zero, one, or two, and $R_{17}$ is as defined below;

and, when $X_1$ is =N—,
- (h) 1-hydroxy-1-cyclohexyl; or
- (i) 1-cyclohexen-1-yl;

with the proviso that $R_4$ contains a sulfur atom only when $X_1$ is =N—;
wherein $R_5$, $R_{15}$ and $R_{25}$ and $R_{35}$ are the same or different and are
  - (i) 2,3, or 4 pyridinyl, or
  - (ii) phenyl substituted by zero to 2 chloro, fluoro, bromo, alkyl of from one to 3 carbon atoms, or alkoxy of from one to 3 carbon atoms, or
  - (iii) phenyl substituted by one trifluoromethyl and zero to one of the previous phenyl substituents, wherein $R_6$ is:
- (a) hydrogen;
- (b) —$OR_{54}$;
- (c) alkanoyloxy of from one to 3 carbon atoms; or
- (d) alkyl of from one to 3 carbon atoms; with the proviso that when m is zero, $R_6$ does not contain oxygen;

wherein $R_7$ is
  - (i) hydrogen,
  - (ii) methyl,
  - (iii) phenylmethyl, or
  - (iv) 2-phenylethyl, wherein $R_8$ is:
  - (i) —$R_{15}$;
  - (ii) —$CH_2R_{15}$, or
  - (iii) —$CHR_{15}R_{25}$;

wherein $R_{17}$ is methyl, phenyl, benzyl, or 2-phenylethyl; and
wherein $R_{54}$ is hydrogen or alkyl of one to 3 carbon atoms;
or an enantiomer or diastereomer of such compound.

Certain compounds of this invention, e.g., those with hydroxyl-bearing $R_4$ groups and those wherein $R_6$ is not hydrogen, have asymmetric carbon atoms and such compounds can exist as enantiomers or diastereomers. Thus all names and representations of compounds as used herein shall include all such isomers and racemic mixtures thereof.

Antiallergy activity is determined by standard laboratory means. One such means employs the passive cutaneous anaphylaxis (PCA) test which is readily accepted as a standard for antiallergy activity, which is described in J. Goose et al., Immunology, 16, 749 (1969) and H. G. Johnson, et al., Agents and Actions 9:235-238 (1979), and is similar to that described in U.S. Pat. No. 4,115,572.

The compounds of this invention were determined to have antiallergy activity by this Rat PCA test procedure as described below.

Rat homocytotropic antibody is elicited to egg albumin (EA) by the injection of 0.5 mg EA+0.5 cc H. pertussis vaccine per rat. After 20-30 days the serum is collected and frozen until used. The antibody is shown to be of 72-hr latency, heat labile type. 0.1 ml of an appropriate dilution of this serum is inoculated into the shaved dorsal surface of a 250 g female Sprague-Dawley (SD) rat. Saline and disodium chromoglycate (DSCG) controls are also run. After 72 hr, the rat is challenged intravenously with 3 mg EA and 5 mg Evans Blue dye. In the case of drug treated animals, the test compound in saline or 0.25% methyl cellulose is given by oral intubation at 20, 60, and 120 minutes prior to challenge with antigen. Results are reported as the number of spots per animal (regardless of size) that are seen at 4 dilutions of serum. The control spots are compared to drug treated spots and spot scores are obtained (number of total spots divided by number of animals). The percent inhibition of the PCA reaction is then calculated. The reproducibility of this assay with repeated testing is approximately 8% for DSCG (IC$_{50}$=Inhibitory Concentration 50%=2.4 mg/kg).

By virtue of this anti-allergy activity the compounds of Formula I are useful in treating AHR symptoms in humans and animals. A physician or veterinarian of ordinary skill readily determines a subject who is exhibiting AHR symptoms. Regardless of the route of administration selected, the compounds of the present invention are formulated into pharmaceutically acceptable dosage forms by conventional methods known to the pharmaceutical art.

The compounds can be administered in such oral unit dosage forms such as tablets, capsules, pills, powders, or granules. They also may be administered rectally, vaginally in such forms as suppositories or bougies; they may also be introduced parenterally, (e.g., subcutaneously, intravenously, or intramuscularly), using forms known to the pharmaceutical art. They are also introduced directly to an affected area, (e.g., in the form of eye drops or by inhalation). For the treatment of AHR induced conditions such as erythema, the compounds of the present invention may also be administered topically in the form of ointments, creams, gels or the like. In general, the preferred route of administration is orally.

An effective but non-toxic quantity of the compound is employed in treatment. The dosage regimen for preventing or treating AHR by the compounds of this invention is selected in accordance with a variety of factors including the type, age, weight, sex, and medical condition of the mammal, the severity of the AHR, the route of administration and the particular compound employed. An ordinarily skilled physician or veterinarian will readily determine and prescribe the effective amount of the anti-AHR agent to prevent or arrest the progress of the condition. In so proceeding, the physician or veterinarian could employ relatively low dosages at first, subsequently increasing the dose until a maximum response is obtained.

Initial dosages of the compounds of the invention are ordinarily in the area of 0.1 mg/kg up to at least 100 mg/kg per dose orally, preferably 5 to 25 mg/kg orally and are given from one to four times daily or as needed. When other forms of administration are employed equivalent doses as administered. When dosages beyond 100 mg/kg are employed, care should be taken with each subsequent dose to monitor possible toxic effects.

The compounds of this invention can also be administered as pharmacologically acceptable acid addition salts such as the hydrochloride, hydrobromide, hydroiodide, sulfate, phosphate, acetate, propionate, lactate, maleate, malate, succinate, tartrate, cyclohexanesulfamates, methanesulfonates, ethanesulfonates, benzenesulfonates, toluene-sulfonates and the like. Additionally, the compounds of this invention may be administered in a suitable hydrated form.

The following procedures are used to establish antihypertensive activity.

Sprague Dawley-specific pathogen-free female rats are prepared for measuring blood pressure directly from a chronic indwelling cannula in the abdominal aorta (see Weeks and Jones, Proc. Soc. Exptl. Biol. Med., 194, 646 (1960)).

Two unanesthetized rats are each given single 50 mg/kg oral doses of the test compound (suspended in a suitable vehicle for administration at 10 cc per kg). Mean arterial blood pressure and cardiac rate are measured before administration and at 4 and 24 hours after administration.

Blood pressure and cardiac rates of the two animals are averaged at each of the three measurement times. If the average decrease at either 4 or 24 hours is 5 mm Hg, or more, the test compound is considered active.

When employing these compounds as antihypertensives, dosages, routes of administration and formulations are employed as previously described for treating AHR symptoms.

The novel compounds of Formula I are named as imidazoles and triazoles by virtue of the presence of two or three heterocyclic nitrogen atoms in a five membered ring. When $X_1$ is nitrogen in Formula I, the heterocyclic ring is a triazole. The heterocyclic ring is numbered clockwise 1–5 starting with $X_1$, as depicted in Formula V. By virtue of the fact that nitrogen atoms are at the 1, 2, and 4 position these compounds are called 1,2,4 triazoles. When $X_1$ contains a carbon atom, the heterocyclic ring is an imidazole. This heterocyclic ring is numbered counterclockwise from 1 to 5 starting with the saturated nitrogen such that $X_1$ is in the 4 position, as depicted in Formula VI. Thus, if $R_1$ is 2-phenylethylamino, $R_4$ is methyl, $R_5$ is phenyl, $R_6$ is hydrogen, $X_1$ is =N—, m is 1, and n is zero, the compound is named 5-methyl-4-phenyl-N-(2-phenylethyl)-4H-1,2,4-triazole-3-ethanamino. If $R_1$ is N-methyl-β-phenethylamine, $R_4$ is methyl, $R_5$ is phenyl, $R_6$ is hydrogen, $X_1$ is =CH—, m is 1 and n is zero, the compound is named N,5-dimethyl-1-phenyl-N-(2-phenylethyl)-1H-imidazoleethanamine.

Certain compounds within the scope of Formula I are preferred, since they have a more advantageous pharmacologic effect.

Thus, compounds of the Formula I, wherein n is zero and $R_6$ and $R_7$ are hydrogen are preferred. More preferred are compounds of the Formula I wherein n is zero, $R_6$ and $R_7$ are hydrogen, m is one or two, and $R_4$ is hydrogen, methyl, hydroxymethyl, $S(O)_qR_{17}$ wherein q is zero, or —CH($R_{35}$)(OH), wherein $R_5$ and $R_{35}$ are phenyl substituted by zero to 2 chloro, fluoro or bromo. Especially preferred are compounds of the Formula I, wherein $X_1$ is =N—, n is zero, $R_6$ abd $R_7$ are hydrogen, m is one or two, and $R_4$ is hydrogen, methyl, hydroxymethyl, $S(O)_qR_{17}$ wherein q is zero, or —CH($R_{35}$)(OH), wherein $R_5$ and $R_{35}$ are phenyl substituted by zero to 2 chloro, fluoro, or bromo.

Examples of alkyl of one to three carbon atoms, inclusive, are methyl, ethyl, and propyl and isomeric forms thereof.

Examples of alkoxy of one to three carbon atoms, inclusive, are methoxy, ethoxy, and propoxy and isopropoxy.

The compounds of this invention are synthesized as illustrated in Charts A–M. Throughout these charts $X_1$, m, n, p, q, $R_1$, $R_4$, $R_5$, $R_6$, $R_7$, $R_8$, $R_{17}$, $R_{35}$, and $R_{54}$ are each defined as above. Additional variables as used in the charts and elsewhere in this specification are defined as follows:

$R_{11}$, $R_{41}$ and $R_{51}$ are the same or different and are hydrogen or methyl;

$R_{13}$ is hydrogen or a suitable oxygen protecting group;

$R_{14}$ is hydrogen, alkyl of one to three carbon atoms, inclusive, $R_{35}$, $CH_2OR_{13}$, $CH_2OR_{26}$;

$R_{16}$ is hydrogen, $OR_{13}$, alkyl or one to three carbon atoms, inclusive, alkyloxy or one to three carbon atoms, inclusive; $R_{21}$ is hydrogen, methyl, or ethyl;

$R_{24}$ is $R_{14}$, $R_{54}$—CH$(CH_2)_m$OR$_{13}$, or 1-cyclohexen-1-yl;

$R_{26}$ is alkyl of one to three carbon atoms, inclusive;

$R_{34}$ is $R_{14}$, or when X is =N—, 1-cyclohexen-1-yl, or $SR_{17}$;

$R_{44}$ is hydrogen or $S(O)_qR_{17}$;

$R_{54}$ is hydrogen or alkyl of one to three carbon atoms, inclusive;

k is zero or, when $R_{54}$ is hydrogen, zero or one.

Examples of suitable oxygen protecting groups are benzyl, t-butyldimethylsilyl, ethoxyethyl and the like. Protection of an N—H containing $R_1$ moiety is necessary for some of the processes described herein for the preparation of compounds of this invention. Suitable nitrogen protecting groups are benzyl, triphenylmethyl, trialkylsilyl, trichloroethylcarbamate, trichloroethoxycarbonyl, vinyloxycarbonyl, vinylcarbamate and the like. Introduction and removal of such suitable oxygen and nitrogen protecting groups are well known in the art of organic chemistry: see, for example, (1) "Protective Groups in Organic Chemistry", J. F. W. McOmie, ed.; (New York, 1973), pages 43ff, 95ff; (2) J. F. W. McOmie, Advances in Organic Chemistry, Vol. 3, pages 191–281 (1963); (3) R. A. Borssonas, Advances in Organic Chemistry, Vol. 3, pages 159–190 (1963); and (4) J. F. W. McOmie, Chem. & Ind. 603 (1979).

Under certain circumstances it is necessary to protect two different oxygens with dissimilar protecting groups such that one can be selectively removed while leaving the other in place. The benzyl and t-butyldimethylsilyl groups are used in this way; either is removable in the presence of the other, benzyl being removed by catalytic hydrogenolysis, and t-butyldimethylsilyl being removed by reaction with, for example, tetra-n-butylammonium fluoride.

In the processes described herein for the preparation of compounds of this invention, the requirements for protective groups are generally well recognized by one skilled in the art of organic chemistry, and accordingly the use of appropriate protecting groups is necessarily implied by the processes of the charts herein, although not expressly illustrated.

The products of the reactions described herein are isolated by conventional means such extraction, distillation, crystallization, chromatography, and the like. Suitable solvents for Grignard or organolithium reactions are (preferably dry) diethyl ether, tetrahydrofuran, dimethoxyethane, inert hydrocarbon solvents, and the like, or mixtures thereof.

The synthesis of imidazole intermediates of Formula XIV is illustrated in Chart A. An isocyanate of the Formula XI is treated with an amino ketal of the Formula III in absolute ethanol and, following the initial exothermic reaction, the mixture is refluxed for a time (e.g. 0.5 to 2 hours) sufficient to produce a thiourea of the Formula XII. The Formula XII thiourea is suspended in warm 10% aqueous hydrochloric acid and refluxed for a time (e.g., 0.5 and 2 hours) sufficient to form a mercaptoimidazole of the Formula XIII, which is oxidatively desulfuized by heating in 20% aqeuous nitric acid on a steam bath to afford an imidazole intermediate of the Formula XIV. Alternatively mercaptoimidazole XIII is desulfurized with Raney-Nickel in refluxing ethanol to produce the imidazole intermediate of the Formula XIV.

The synthesis of triazole intermediates of the formulas XXIV and XXV is illustated in Chart B. An isothiocyanate of the Formula XXI is treated with a hydrazide of the Formula IV in ethanol and, following the initial exothermic reaction, the mixture is refluxed for a time (e.g., 0.5 to 2 hours) sufficient to yield a compound of the Formula XXII. A Formula XXII compound is treated with warm 5 to 20% aqeuous sodium hydroxide solution and refluxed for a time (e.g., 0.5 to 2 hours) sufficient to generate a mercaptotriazole of the Formula XXIII, which is desulfurized, using either of the methods described above, to give a triazole of the Formula XXIV.

When $R_{24}$ of the Formula XXIII compound is hydrogen the sulfur is alkylated by reaction wih a base and a suitable alkyl chloride, bromide or iodide of the Formula $R_{17}$—X, wherein X is chloro, bromo, or iodo, to produce a compound of the Formula XXV.

In Chart C are illustrated the preparations of certain imidazoles and triazoles of this invention of the formulas, XXXV and XXXIX, and of alcohol intermediates of the Formulas, XXXII, XXXVII, and XXXVIII. A compound of the Formula XXXI is heated with paraformaldehyde in a hydrocarbon solvent to produce a hydroxymethyl compound of the Formula XXXII, which is oxidized with manganese dioxide to afford an aldehyde of the Formula XXXIII. Reaction of the Formula XXXIII aldehyde with either dimethylsulfonium methylide in dimethylsulfoxide at 20° to 25° C. or diazomethane in methanol affords an epoxide of the Formula XXXIV. The Formula XXXIV epoxide is treated with an amine of the Formula, $R_1H$, in tetrahydrofuran solution, optionally in the presence of potassium iodide (preferably 1 equivalent), to give a compound of the Formula XXXV.

Reaction of a compound of the Formula XXXI with n-butyllithium in tetrahydrofuran or 1,2-dimethoxyethane-hexane mixture at −20° to 0° C. generates the lithiated intermediate of the Formula XXXVI, which is treated with excess ethylene oxide at 5° to 25° C. for 5 to 24 hours to prepare a compound of the Formula XXXVII.

Treating the aldehyde of the Formula XXXIII with a suitable Grignard or alkyllithium reagent in a suitable solvent yields an alcohol of the Formula XXXVIII.

Treating the aldehyde XXXIII with a Grignard reagent of the Formula Br-or Cl—$MgCH_2CH_2CH_2R_1$ (prepared in the usual way) in a suitable solvent affords a compound of the Formula XXXIX.

The process illustrated in Chart D is used to prepare imidazoles and triazoles of this invention of the Formula XLV. An aldehyde of the Formula XLI is treated with a vinyl Grignard or vinyllithium reagent in a suitable solvent to produce an allylic alcohol of the Formula XLII, which is oxidized with a suitable reagent such as manganese dioxide or chromium trioxide to produce an enone of the Formula XLIII. Michael-type addition of an amine of the formula, $R_1H$, to a Formula XLIII enone affords a ketone of the Formula XLIV, which is reduced under suitable conditions for example with sodium borohydride, diborane, or sodium bis(2-methoxyethoxy)aluminumhydride to give an alcohol of the Formula XLV.

The process of Chart E is used to prepare imidazoles and triazoles of the Formula LII. An alcohol of the Formula LI is treated with a suitable base such as sodium hydride in a solvent such as dimethylformamide, followed by treatment with an appropriate alkyl halide of the formula, $R_{26}Cl$, $R_{26}Br$, or $R_{20}I$, to yield a Formula LII compound.

The process of Chart F is used to prepare triazole intermediates of the Formulas, LXII, LXII, and LXIV. A mercapto compound of the Formula LXI (which is within the scope of Formula XXIII of Chart B and prepared as depicted therein), is treated with a suitable base and a suitable $R_{17}$ halide of the Formula $R_{17}Cl$, $R_{17}$—Br, or $R_{17}$—I to give a sulfide of the Formula LXII. Oxidation of a sulfide of the Formula LXII under suitable conditions for example, with aqueous hydrogen peroxide or preferably with one equivalent of m-chloroperbenzoic acid in methylene chloride or chloroform, produces a sulfoxide of the Formula LXIII, which can be further oxidized, for example, with m-chloroerbenzoic acid at 25° C. for 24 hours to generate a sulfone of the Formula LXIV.

Imidazoles and triazoles of this invention of the Formula LXXIII are prepared using the process of Chart G. An alcohol of the Formula LXXI (which is within the scope of Formulas XXXII, XXVII, and XXXVIII of Chart C and is prepared as depicted therein), is stirred and treated with an excess (for example, 1.2 equivalents) of methanesulfonyl chloride in the presence of an excess (for example, 1.5 equivalents) of triethylamine in a suitable solvent such as methylene chloride, chloroform, or tetrahydrofuran for a time (e.g., 0.5 to 2 hours) sufficient to give a methanesulfonate ester of the Formula LXXII. A Formula LXXII ester is treated with an excess (for example 2 equivalents) of potassium iodide followed by an excess (for example 2.2 equivalents) of an amine of the Formula $R_1H$ in a suitable solvent such as tetrahydrofuran, 1,2-dimethoxyethane, or chloroform, for 10 to 24 hours at elevated temperature, for example, at the reflux temperature of the mixture, to afford an amine of the Formula LXXIII.

Triazoles of this invention of the Formula LXXXIII are prepared as illustrated in Chart H by a process analogous to that described for Chart G. An alcohol of the Formula LXXXI is converted to a methanesulfonate ester of the Formula LXXXII, which is then converted to an amine of the Formula LXXXIII.

The processes of Chart I are used to prepare triazoles of this invention of the Formulas, XCII, XCIII, XCIV, XCV, XCVI, XCVII, XCVIII and XCIX. A triazole of the Formula XCI is treated with one to two equivalents of n-butyllithium in a suitable solvent such as a 1,2-dimethoxyethane-hexane mixture or tetrahydrofuran at −60° to 0° C. to form a lithiated intermediate compound of the Formula XCII. A Formula XCII intermediate is reacted with a disulfide of the formula, $R_{17}$—S—S—$R_{17}$, to afford a sulfide of the Formula XCIII, which can be oxidized, by processes described above, to yield in turn a sulfoxide of the Formula XCIV and a sulfone of the Formula XCV. Treating the Formula XCII intermediate with sulfur gives a mercaptotriazole of the Formula XCVI. Treating a Formula XCII intermediate with cyclohexanone produces a compound of the Formula XCVII. Treating a Formula XCII intermediate with an aldehyde of the Formula $R_{35}CHO$ generates a compound of the Formula XCVIII. Treating the Formula XCII intermediate with an alkyl halide of the Formula $R_{26}Cl$, $R_{26}Br$ or $R_{26}I$ produces a triazole of the Formula XCIX.

The processes of Chart J are used to prepare imidazoles and triazoles of this invention of the formulas CIV and CV. An alcohol of the Formula CI (wherein m is one to 3 inclusive) is oxidized under suitable conditions, for example, Pfitzner-Moffatt conditions (dimethylsulfoxide, phosphoric acid and a carbodiimide) or with dimethylsulfoxide and oxalyl chloride, to afford a ketone of the Formula CII. Reaction of a ketone CII with a Wittig reagent of the Formula $R_{41}C$—$(R_{51})$=P(-phenyl)$_3$ produces an olefin of the Formula CIII, which is hydrogenated to yield a compound of the Formula CIV (wherein m is one to 3 inclusive). Wolff-Kishner reduction of a ketone of the Formula CII (wherein m=one to 3 inclusive) gives a compound of the Formula CV. As an alternative a ketone of the Formula CII is converted to a dithioketal, which is desulfurized with Raney-Nickel to generate a compound of the Formula CV, using a process similar to that described in J. R. Lindsay Smith, et al., Journal of the Chemical Society, Perkin I, page 2863 (1979).

The processes of Chart K are used to prepare imidazoles of this invention of the Formula CXIII. An alcohol of the Formula CXI is oxidized under suitable oxidizing conditions, for example, as described above, or with manganese dioxide to afford an aldehyde of the Formula CXII, which is treated with a suitable $R_{35}$-containing Grignard or organolithium reagent to produce an imidazole of the Formula CXIII.

The process of Chart L is used to prepare imidazoles and triazoles of this invention of the Formula CXXII except when $R_4$ is -SH (mercapto)-see Chart M. An alcohol of the Formula CXXI is esterified to yield a Formula CXII ester under standard conditions well known in the art, for example, with an appropriate acid chloride in pyridine, or with an acid anhydride or mixed anhydride in tetrahydrofuran, or the like.

The process of Chart M is used to produce triazoles of this invention of the Formula CXXXIII. A compound of the Formula CXXXI is esterified under conditions well known in the art, for example, as described for Chart L to give a compound of the Formula CXXXII, which is selectively hydrolyzed with one equivalent of a suitable base to afford a compound of the Formula CXXXIII.

The starting materials required for the processes described in this invention are either commercially available or they can be synthesized by methods known in the art of organic chemistry. For example, the isothiocyanates of the Formula XI (or XXI) are generally available commercially, or they can be made by the reaction of an appropriate primary amine with N,N'-thiocarbonyldiimidazole. Intermediates of the Formula III are prepared by methods described in U.S. Pat. No. 3,992,408 or British Pat. No. 1,456,946. Intermediate hydrazides of the Formula IV are available commercially or they can be made from hydrazine and a suitable activated derivative of the appropriate carboxylic acid. The amines $R_1H$ are available commercially, are known, or can be prepared by methods well known in the art of organic chemistry. The intermediate aldehydes, $R_{35}CHO$, are either known or they can be prepared by the reaction of an appropriate $R_{35}$-containing Grignard or organolithium reagent with trimethylorthoformate followed by hydrolysis.

The acid addition salts of the Formula I compounds are prepared by reacting the amino base with the stoichometric equivalent of the acid correspond-ing to the pharmacologically acceptable acid addition salt.

The compounds of this invention may also exist in hydrated or solvated forms.

DESCRIPTION OF THE PREFERRED EMBODIMENTS

The operation of this invention is further elaborated by the representative examples below:

EXAMPLE 1

5-Methyl-4-phenyl-N-(2-phenylethyl)-4H-1,2,4-triazole-3-ethanamine, dihydrochloride monohydrate (Formula LXXIII of Chart G: $R_1$ is phenylethylamine, $R_{44}$ is methyl, $R_5$ is phenyl, $R_{54}$ is hydrogen, $X_1$ is nitrogen, k is one and n is zero)

Refer to Charts B, C, and G.

A. 3-Methyl-4-phenyl-4H-1,2,4-triazole (Formula XXIII of Chart B)

2.5 mol of phenyl isothiocyanate (Formula XXI of Chart B) is added to 0.5 mol of acethydrazide (Formula IV of Chart B) in 500 ml of absolute ethanol and refluxed for one hour, cooled and filtered. This is then dissolved in a solution of 28.0 gm sodium hydroxide in 400 ml of water and the mixture is refluxed for two hours. The reaction mixture is cooled in an ice bath and treated with 100 ml of concentrated hydrochloric acid. The resulting solid is filtered and recrystallized. 66.7 mmol of the solid is added to 53 ml of 20% nitric acid and heated on a steam bath. When the vigorous exothermic reaction is complete, an additional 53 ml of 20% nitric acid is added, and an additional 66.7 mmol of previous solid. Portions of the solid are reacted with nitric acid until all of the previous solid is reacted. After the final addition the reaction mixture is heated twenty minutes on a steam bath, cooled to ambient temperature and poured into cold 15% aqueous ammonium hydroxide solution. The subtitled product is extracted with chloroform, dried and concentrated to yield 3-methyl- 4-phenyl-4H-1,2,4-triazole, (Formula XXIV, Chart B) mp 109°–111° C.

B. 4-Phenyl-5-methyl-3-hydroxyethyl-4-H-1,2,4-triazole (Formula XXXVII of Chart C).

31.8 g (0.20 mol) of 5-methyl-4-phenyl-4H-1,2,4-triazole is dissolved in 100 ml of tetrahydrofuran and slowly added to 140 ml of 1.6 M n-butyl lithium in 500 ml of tetrahydrofuran in a 2 liter, 2-neck flask with magnetic stirrer at −60° C. It is necessary to add an additional 250 ml of tetrahydrofuran to prevent crystallization. The reaction mixture is stirred for two hours at −60° C., at which time 230 ml of 4.55 M solution of ethylene oxide in tetrahydrofuran is added. The mixture is maintained at 0° to 6° C. for fifteen hours. The mixture is then quenched by adding 100 ml of a saturated aqueous sodium bicarbonate solution and concentrated in vacuo. The resulting mixture is taken up in a chloroform/aqueous sodium bicarbonate mixture and extracted with chloroform, dried over sodium sulfate and concentrated to yield 33.8 g of oil. The oil is chromatographed over silica gel in a methanol/chloroform concentrated ammonia solvent system and 20 ml fractions taken. Fractions 101–361 were combined to yield 12.3 gm of the subtitled product having a melting point of 136°–138° C.

C. 5-Methyl-4-phenyl-N-(2-phenylethyl)-4H-1,2,4-triazol-3-ethaneamine, dihydrochloride monohydrate (Formula LXXIII of Chart G)

Methanesulfonyl chloride (1.2 equiv.) in 2.5 ml of methylene chloride at zero degrees is added to 3.05 g of 4-phenyl-5-methyl-3-hydroxyethyl-4H-1,2,4-triazole in 50 ml of methylene chloride and 2.25 g of triethylamine. The reaction mixture is stirred for two hours and quenched in cold aqueous sodium bicarbonate, then extracted with methylene chloride. The extract is dried over sodium sulfate, filtered and is concentrated in vacuo yielding the Formula XVII mesylate. The mesylate is taken up in 60 ml of tetrahydrofuran and 2.49 gm of potassium iodide is added followed by 5.50 gm of phenethylamine. The mixture is heated to 60° C. for eighteen hours. The reaction mixture is extracted with methylene chloride and dried over sodium sulfate and concentrated in vacuo to yield 8.4 g of Formula XLIII product. This is chromatographed over silica gel and 20 ml fractions are taken. Fractions 70–90 are combined to give 4.7 g of an oil. The oil is crystallized as the HCl salt from methanol, acetone, ethyl/acetate solvent system, yielding 3.37 gm of crystals of the titled product, having a melting point of 194°–198° C. The Carbon:Hydrogen:Nitrogen ratio is 57.81:6.35:14.13.

Infrared absorptions are observed at 3186, 1600, 1590, 1533 and 1502 cm$^{-1}$. NMR absorptions are observed at 7.5–7.7, 7.2–7.4, 4.24, 3.95, 2.74 and 2.25 $\delta$. The mass spectrum exhibits peaks at m/e 203, 174, 173, 172, 131, 118, 107, 97, 91, 79, 77 and 51.

EXAMPLE 2

N,5-Dimethyl-4-phenyl-N-(2-phenylethyl)-4H-1,2,4-triazole-3-ethanamine, monohydrobromide (Formula LXXIII of Chart G: $R_1$ is N-methylphenethylamino, $R_5$ is phenyl, $R_4$ is methyl, $R_{54}$ is hydrogen, $X_1$ is nitrogen, k is one and n is zero). Refer to Chart G.

The mesylate is prepared as described in Example 1, part C (Formula LXXII, Chart G), is taken up on 40 ml of tetrahydrofuran with appropriate amounts of potassium iodide and N-methylphenethylamine and heated to 60° C. for eighteen hours. The mixture is subsequently quenched in aqueous sodium hydroxide and extracted with chloroform, then it is dried over sodium sulfate and concentrated in vacuo and then with a pump to yield 2.54 gm of a tan oil. The oil is chromatographed over silica gel and 20 ml fractions taken. Fractions 20–40 are combined to yield 2.08 g of a colorless oil. The hydrobromide salt is crystallized from an acetone/hexane solvent system to yield 1.87 g of the titled product having a melting point of 130° to 132° C. The Carbon:Hydrogen:Nitrogen ratio is 59.80:6.31:14.03.

Infrared absorptions are observed at 2582, 2545, 2445, 1601, 1588, 1536, 1517, 1504, 1494 and 697. NMR absorptions are observed at 2.84, 2.18, 2.9–3.6, 7.2, and 7.6–8.8 $\delta$. The mass spectrum exhibits peaks at m/e 230, 229, 186, 185, 148, 105, 91, 77, 44 and 42.

EXAMPLE 3

1-[2-(5-Methyl-4-phenyl-4H-1,2,4-triazol-3-yl)ethyl]-4-phenyl-piperazine (Formula LXXIII of Chart G: $R_1$ is 4-phenyl piperazine, $R_{44}$ is methyl, $R_5$ is phenyl, $R_{54}$ is hydrogen, $X_1$ is -N-, k is one and n is zero).

Refer to Chart G.

The mesylate is prepared as described in Example 1, part C (Formula LXXII, Chart G), is quenched in cold aqueous sodium bicarbonate, extracted with methylene chloride, dried over sodium sulfate and concentrated in vacuo to yield an oil. The oil is dissolved in 40 ml of tetrahydrofuran treated with 3.32 g of potassium iodide, and 5.36 gms of 1-phenylpiperazine and heated to 60° C. for eighteen hours. The mixture is subsequently quenched in aqueous sodium hydroxide and extracted with chloroform. Then it is dried over sodium sulfate and concentrated in vacuo to form an oil. The oil is chromatographed over silica gel and 20 ml fractions are collected. Fractions 21–40 are combined and concentrated to form a solid. The free base is crystallized from a tetrahydrofuran/hexane mixture to give 2.29 g of the titled product having a melting point of 116°–118° C. Carbon:Hydrogen:Nitrogen ratio is 72.36:7.25:20.40.

Infrared absorptions are observed at 1598, 1579, 1532, 1521, 1504, 1495, 1377, 1231, 1137, 1014, 768, and 696. NMR absorptions are observed at 2.16, 2.5, 3.2, 2.76, 6.8, 7.2 and 7.6 $\delta$. The mass spectrum exhibits peaks at m/e 216, 215, 186, 173, 145, 132, 104, 77, 70 and 42.

EXAMPLE 4

1-(4-Fluorophenyl)-4-[2-(5-methyl-4-phenyl-4H-1,2,4-triazole-3-yl)ethyl]piperazine (Formula LXXIII of Chart G: $R_1$ is 4-fluorophenylpiperazinyl, $R_{34}$ is methyl, $R_5$ is phenyl, $R_{54}$ is hydrogen, $X_1$ is nitrogen, k is one and n is zero).

Refer to Chart G.

The mesylate is prepared as described in Example 1, part C (Formula LXXII, Chart G), quenched in cold aqueous sodium bicarbonate, extracted with methylene chloride, dried over sodium sulfate and concentrated in vacuo to yield an oil. The oil is dissolved in 40 ml of tetrahydrofuran treated with 3.32 g of potassium iodide and 4.00 g of 1-(p-fluorophenyl)piperazine and heated to 60° C. for eighteen hours. The mixture is subsequently quenched in aqueous sodium hydroxide and extracted with chloroform. It is then dried over sodium sulfate and concentrated in vacuo to form an oil. Fractions 58–77 are combined and concentrated to 3.72 g of a light yellow oil. Crystallization from appropriate solvents yields 2.4 g of the titled product having a melting point of 101°–104° C. The Carbon:Hydrogen:Nitrogen ratio is 68.96:6.87:19.45.

Infrared absorptions are observed at 3040, 1600, 1595, 1530, 1510, 1240, 835, 825, and 700. NMR absorptions are observed at 2.25, 2.8, 6.8–7.0, 7.25 and 7.6 δ. The mass spectrum exhibits peaks at m/e 229, 216, 215, 186, 173, 163, 150, 122, 70 and 42.

EXAMPLE 5

1-[2-(5-methyl-1-phenyl-1H-imidazol-2-yl)-ethyl]-4-phenyl-piperazine (Formula LXXIII of Chart G: $R_1$ is N-phenylpiperazine, $R_{34}$ is methyl, $R_5$ is phenyl, $R_{54}$ is hydrogen, $X_1$ is =CH—, k is one and n is zero).

Refer to Charts A, C, and G.

100 mmol of phenol isothiocyanate is added to 100 mmol of aminoacetone-ethylene glycol ketal dissolved in 110 ml of absolute ethanol. The resulting mixture is refluxed for 30 min, cooled to below room temperature and filtered. The resulting crude thiourea (mp 133.5°–135° C. and Carbon:Hydrogen-Nitrogen ratio of 57.15:6.29:11.12:13.17) is suspended in 550 ml of 10% aqueous hydrochloric acid and refluxed for 1 hr. The resulting solid is filtered, washed with water and ethyl acetate, and recrystallized from 500 ml of methanol-/ethyl acetate to yield crystals with a melting point of 249°–252° C. The Carbon:Hydrogen-Nitrogen:Sulfur ratio is 62.81:5.27:14.65:15.74.

66.7 mmol of this thioimidazole is cautiously added to 53 ml of 20% nitric acid and heated on a steam bath. After 20 min, the mixture is cooled to ambient temperature and poured into ice cold 15% aqueous ammonium hydroxide solution. The product is extracted with chloroform, dried and concentrated to an oil.

After several repetitions of this procedure, 179 mmol of this product is dissolved in 180 ml of THF. The mixture is treated under nitrogen with 100 ml of 1.64 molar n-butyllithium in hexane (0.164 mol). The solution is stirred for ¾ of an hr, warmed to 0° C., stirred for ½ hr, treated with 16 ml more of 1.64 molar n-butyllithium (0.026 mol) and cooled to −78° C. The anion thus formed is treated with 140 ml of a 9.1 molar solution of ethylene oxide in THF and the reaction is warmed to 0° C. Stirring is maintained at 0° C. for 2 hr after which the reaction temperature is permitted to rise overnight. The reaction is quenched in aqueous sodium hydroxide solution, extracted with chloroform, dried over sodium sulfate and concentrated in vacuo to an oil. The oil is chromatographed on 1750 g of silica gel using 9 liters of 5–8% methanol/chloroform which is collected in 20 ml fractions. Fractions 131–270 are concentrated to yield 16.4 g of 2-hydroxyethyl-4-methyl-3-phenylimidazole crystals having a melting point of 130°–134° C. The Carbon:Hydrogen:Nitrogen ratio is 71.26:6.58:13.98.

An imidazole mesylate (Formula LXXII of Chart G) is prepared by adding methanesulfonyl chloride in 15 ml of methylene chloride at 0° C. to 2.02 g of 2-hydroxyethyl-4-methyl-3-phenylimidazole dissolved in 40 ml of methylene chloride and 2.06 ml of triethylamine. The reaction mixture is stirred for fifteen minutes at 0° C., then quenched in cold aqueous sodium bicarbonate, extracted with methylene chloride and concentrated in vacuo. The concentrate is taken up in 40 ml of tetrahydrofuran and 3.32 g of potassium iodide is added, followed by 3.60 g of N-phenylpiperazine. The solution is heated to reflux for thirteen hours, then stirred at ambient temperature for three days. The reaction mixture is extracted with methylene chloride and dried over sodium sulfate and concentrated to yield a semisolid. The semisolid is chromatographed over silica gel and 2nd and 3rd 200 ml fractions are combined and concentrated to a solid. The solid is crystallized from tetrahydrofuran/hexane/diethylether solvent system to give the titled product with a melting point of 109.5°–111° C. The Carbon:-Hydrogen:Nitrogen analysis is 76.17:7.56:16.04.

Infrared absorptions are observed at 3090, 3050, 2760, 1630, 1605, 1600, 1585, 1580, 1570, 1495, 1240, 1150, 815, 765 and 700. NMR absorptions are observed at 2.0, 2.5, 3.1, 2.74, 6.8–7.5 δ. The mass spectrum exhibits peaks at m/e 228, 215, 214, 185, 175, 172, 161, 145, 132 and 70.

EXAMPLE 6

1-[4-fluorophenyl-4-[3-(4-phenyl-4H-1,2,4-triazol-3-yl)propyl]piperazine (Formula LXXXIII of Chart H: $R_1$ is N-(4-fluorophenyl)piperazinyl, $R_{44}$ is hydrogen, $R_5$ is phenyl, $R_{54}$ is hydrogen, $X_1$ is —N—, m is two and n is zero).

Refer to Charts B, C and H.

Following the procedure in Example 1, Parts A and B which is outlined in the specification and on Charts B and C, but employing ethanohydrazide in place of acethydrazide in Part A, 3-hydroxypropyl-4-phenyl-5-mercapto-1,2,4-imidazole is prepared, having a melting point of 191°–193° C. and a Carbon:Hydrogen:Nitrogen:Sulfur ratio 56.16:5.59:17.87:13.61. 3-hydroxypropyl-4phenyl-1,2,4-imidazole of Formula XXXII of Chart C is then prepared, having a melting point of 101°–103° C. and a Carbon:Hydrogen:Nitrogen ratio of 65.00:6.45:20.68. A triazole mesylate is subsequently prepared from this product by the method described in Example 1 by treating this compound with 1.2 equivalents of methane sulfonyl chloride. 2.17 g of this solid mesylate (Formula LXXXII, Chart H) is suspended in 30 ml tetrahydrofuran. This is treated with 3.36 g of potassium iodide and 4.0 g of 1-(p-fluorophenyl)piperazine. The mixture is heated to reflux overnight. The reaction mixture is extracted with methylene chloride, dried over sodium sulfate and concentrated in vacuo and left to stand for three days. The resulting semisolid is chromatographed over silica gel and 20 ml portions obtained. Fractions 55–67 are combined and concentrated in vacuo to yield 3.1 g of an oil which is crystallized from appropriate solvent to yield 1.74 g of the titled crystalline prisms having a melting point of 104°–106° C. The Carbon:Hydrogen:Nitrogen ratio is 68.75:6.12:18.96.

Infrared absorptions are observed at 3100, 2770, 1725, 1600, 1590, 1575, 1515, 1505, 1240, 1170, 780, 755, 700 and 685. NMR absorptions are observed at 1.92, 2.4, 2.8, 2.7, 6.8, 7.3, 7.5 and 8.16 δ. The mass spectrum exhibits peaks at m/e 215, 186, 159, 158, 105, 104, 91, 77, 51 and 42.

EXAMPLE 7

1-Phenyl-4-[3-(4-phenyl)-4H-1,2,4-triazol-3-yl)-propyl]-piperazone (Formula LXXXIII of Chart H: $R_1$ is N-phenylpiperazinyl, $R_{34}$ is hydrogen, $R_5$ is phenyl, $R_{54}$ is hydrogen, $X_1$ is —N—, m is two and n is zero).

Refer to Chart H.

Following the procedure of Example, an appropriate triazole mesylate (fomula LXXII, Chart H), is dissolved in an appropriate amount of tetrahydrofuran and treated with 6.64 g of potassium iodide and 7.44 g (44 mmole) of N-phenylpiperazine and heated to reflux overnight. The reaction mixture is quenched with sodium hydroxide, extracted with chloroform, dried over sodium sulfate and concentrated in vacuo to an oil. The oil is chromatographed over silica gel and 20 ml fractions are taken. Fractions 68-90 are combined and concentrated to an oil which subsequently solidifies. Crystallization is obtained from ethyl acetate giving colorless needles having a melting point of 131°-133° C. 1.54 g). The Carbon:Hydrogen:Nitrogen ratio is 68.75:6.12:18.96.

Infrared absorptions are observed at 3100, 2810, 2770, 1735, 1615, 1600, 1590, 1515, 1505, 1240, 1140, 1165, 815, 770 and 695. NMR absorptions are observed at 2.9, 2.8, 2.4, 3.0, 6.9, 7.3, 7.5 and 8.16 $\delta$. The mass spectrum exhibits peaks at m/e 241, 216, 215, 207, 186, 179, 172, 150, 158 and 122.

EXAMPLE 8

1-(4-Fluorophenyl)-4-[3-(5-methyl-4-phenyl-4H-1,2,4-triazol-3-yl)propyl]piperazine dihydrochloride monohydrate (Formula XCIX of Chart I: $R_1$ is 1-(4-fluoro-phenylpiperazinyl, $R_{26}$ is methyl, $R_5$ is phenyl, $R_{16}$ is hydrogen, $X_1$ is —N—, m is 2 and n is zero).

Refer to Chart I.

The product of Example 6 (1.83 g), (which corresponds to Formula XCI of Chart I, wherein $R_5$ is phenyl, m is 2, $R_{16}$ is hydrogen, and $R_1$ is 1-(4-fluorophenylpiperazinyl), is dissolved in 15 ml of tetrahydrofuran in a 2-neck flask and is treated with 1 mg bipyridyl and cooled within a salt ice bath for one-half hour. The mixture is then treated with 3.5 ml of n-butyl-lithium at 10° whereupon a purple color develops. The solution is stirred for thirty seconds and quenched with 0.87 g of methyl iodide and stirred for five minutes at which point the purple color disappears. The solution is then quenched with cold aqueous sodium hydroxide and extracted with chloroform. The extract is dried over sodium sulfate and is concentrated in vacuo to yield 2.0 g of crude oil. The oil is chromatographed over silica gel and 20 ml portions taken. Portions 76-81 are combined and concentrated in vacuo to yield an oil which is crystallized from a methanol/diethyl/ether solvent system to yield the HCl salt. The title product is a white powder having a melting point of 167°-187° C. Carbon:Hydrogen:Nitrogen ratio is 56.06:6.41:14.81.

Infrared absorptions are observed at 3400, 3060, 2420, 1625, 1595, 1565, 1505, 1235, 975, 895, 845, 730 and 695. NMR absorptions are observed at 2.4, 2.54, 2.92, 3.4, 3.6, 7.0-7.4, 7.75 $\delta$. The mass spectrum exhibits peaks at m/e 229, 200, 186, 173, 172, 122, 77, 70, 56 and 42.

EXAMPLE 9

5-methyl-1-phenyl-N-(2-phenylethyl)-1H-imidazole-ethanamine, dihydrochloride, hemihydrate (Formula XLIII of Chart D: $R_1$ is phenethylamino, $R_{34}$ is ethyl, $R_5$ is phenyl, $R_{54}$ is hydrogen, $X_1$ is =CH-, k is one and n is zero).

Refer to Chart G.

10.3 g of the mesylate (Formula LXXII of Chart G) of 5-methyl-4-phenyl-1H-imidazole-2-ethanol is prepared as described in Example 5 and dissolved on 120 ml of tetrahydrofuran. To 63 ml of this solution in a flask is added 4.98 gms (30 mmoles) of potassium iodide and 5.50 gms of phenethylamine, and the resulting mixture is heated to 55° C. overnight.

The mixture is quenched in cold aqueous sodium hydroxide and extracted with methylene chloride. The resulting compound is dried over sodium sulfate and concentrated in vacuo to yield 2.42 gms of oil. The oil is crystallized from a methanol acetone diethylether solvent system as the hydrochloride salt to yield 200 mg of the titled crystalline needles having a melting point of 204°-207° C. The Carbon:Hydrogen:Nitrogen ratio is 61.78:6.77:10.85.

Infrared absorptions are observed at 3300, 2720, 2660, 2520, 2460, 1630, 1595, 1585, 1555, 1515, 830, 775, 755, 750 and 700. NMR absorptions are observed at 2.1, 2.9-3.4, 7.3, 7.6, 7.4 $\delta$. The mass spectrum exhibits peaks at m/e 215, 214, 185, 173, 172, 171, 77, 38, 36 and 35.

EXAMPLE 10

N,5-dimethyl-1-phenyl-N-(2-phenylethyl)-1H-imidazole-ethanamine, monohydrochloride (FOrmula XLIII of chart D: $R_1$ is N-methyl-$\beta$-phenethylamine, $R_{34}$ is methyl, $R_5$ is phenyl, $R_{54}$ is hydrogen, $X_1$ is =CH—, and n is zero).

Refer to Chart G.

Following the procedure of Example 5, but employing 4-fluorophenyl-isocyanate in the first step, 1-(4-fluorophenyl)-5-methyl-1H-imidazole-2-ethanol is prepared, having a metling point of 124°-126° C. and a Carbon:Hydrogen:Nitrogen ratio of 65.45:5.95:12.72. The mesylate is prepared as in Example 5.

64 ml of the mesylate solution is placed in a flask and 4.98 gms of potassium iodide (30 mmoles) followed by 5.97 gms of N-methylphenethyl amine is added. After heating to 55° overnight, the solution is then stirred for one day at room temperature and quenched in sodium hydroxide. The resulting mixture is extracted with chloroform, dried over sodium sulfate and concentrated in vacuo to 9.4 gms of an oil. The resulting oil is chromatographed over silica gel, using a methanol chloroform solvent system and 20 ml fractions are collected. Fractions 86-120 are combined to yield a crude oil having a weight of 3.65 gms. This oil is crystallized as the hydrochloride salt from a methanol acetone solvent system yielding 3.42 gms of the titlted crystalline material having a melting point of 205°-207° C. The Carbon:Hydrogen:Nitrogen ratio is 62.96:6.90:10.05.

Infrared absorptions are observed at 3660, 3560, 3480, 3360, 3060, 2600, 1630, 1600, 1550, 1515, 730 and 695. NMR absorptions are observed at 2.1, 2.86, 2.9-3.6, 7.3, 7.65 and 7.44 $\delta$. The mass spectrum exhibits peaks at m/e 229, 228, 185, 149, 148, 105, 77, 44, 42 and 36.

EXAMPLE 11

1-(4-Fluorophenyl)-4-[2-[1-(4fluorophenyl)-5-methyl-1H-imidazol-2-yl]ethyl]piperazine (Formula XLIII of Chart D: $R_1$ is 1-(4-fluorophenyl)piperizinyl, $R_{34}$ is methyl, $R_5$ is 4-fluorophenyl, $R_{54}$ is hydrogen, $X_1$ is =CH—, is one and n is zero).

Refer to Chart G.

Following the procedure of Example 9, 2-hydroxyethyl-4-methyl-3-(4-fluorophenyl)imidazole of Formula XLI of Chart D is prepared and converted to 6.3 gms of the mesylate as described in Example 1, part C. The yellow liquid is dissolved in 20 ml of methylene chloride, 2.4 gms of triethylamine is added, followed by 2.8 gm (21 mmoles) of 1-(4fluorophenyl)piperazine in 10 ml of methylene chloride. The reaction mixture is heated to reflux under a nitrogen atmosphere for four hours and then stirred at room temperature for two days. The solution is then quenched with sodium bicarbonate, dried over sodium sulfate and concentrated in vacuo to yield approximately six grams of an oil. This oil is chromatrahed over silica gel using a methanol chlorofrom solvent system and 20 ml fractions taken. Fractions 55-90 are combined to yield four grams of a yellow oil. This oil is crystallized in an ethyl/acetate-hexane solvent system, to yield 3.1 gm of the titled crystals having a melting point of 1.05° C. The Carbon:Hydrogen:Nitrogen ratio is 69.04:6.22:14.63.

Infrared absorptions are observed at 2780, 1670, 1610, 1600, 1595, 1570, 1515, 1240, 1225, 1155, 850, 820 and 805. NMR absorptions are observed at 2.0, 2.55, 2.75, 6.8-7.0 and 7.28 $\delta$. The mass spectrum exhibits peaks at m/e 232, 202, 193, 190, 179, 163, 150, 122, 95 and 70.

EXAMPLE 12

1-(4-Chlorophenyl)-4[2-[1-(4-fluorophenyl)-5-methyl-1H-imidazol-2-yl]ethyl]piperazine (Formula LXXIII of Chart G: $R_1$ is 4-(4-chlorophenyl)piperizyl, $R_{34}$ is methyl, $R_5$ is 4-fluoromethyl, $R_6$ is hydrogen, $X_1$ is +CH—, k is one and n is 0).

Refer to Chart G.

The mesylate described in Example 11 is prepared from 3.0 gm (13.6 mmoles) of the alcohol, 1.5 gms of triethylamine (15 mmoles) dissolved in 20 ml of methylene chloride chilled to 0° C., and 1. gms of methanesulfonylchloride in 10 ml of methylene chloride. The reaction mixture is allowed to warm to room temperature. An additional 1.5 gms of triethylamine is then added, followed by 2.0 gms (15 mmoles) of 1-(4-chlorophenyl)-piperazine in 10 ml of methylene chloride. The solution is then heated to reflux for forty-eight hours. The solution is cooled and quenched with cold aqueous sodium hydroxide and washed with methylene chloride, dried over sodium sulfate and concentrated in vacuo to an oil. The oil is then chromatographed over silica gel in a methanol, chloroform, solvent system and 20 ml fractions taken. Fractions 45-70 are combined to yield a product having a weight of 1.52 gms. This product is then crystallized from an ethyl acetate hexane solvent system, filtered and washed with hexane to yield 1.1 gms of the titled product having a melting point of 137°-138.5° C. The Carbon:Hydrogen:Nitrogen ratio is 66.37:6.36:14.29.

Infrared absorptions are observed at 3050, 2780, 1685, 1630, 1605, 1575, 1580, 1515, 1495, 1305, 1240, 1225, 1140, 860, 820 and 800. NMR absorptions are observed at 2.0, 2.74, 2.5, 6.8, 6.8-7.2, and 7.2. The mass spectrum exhibits peaks at m/e 233, 232, 209, 195, 190, 179, 95, 70, 42 and 28.

EXAMPLE 13

1-[2-[1-(4-Fluorophenyl)-5-methyl-1H-imidazol-2-yl]-ethyl]-4-phenyliperazine (Formula LXXIII of Chart G: $R_1$ is 4-phenylpiperazyl, $R_{34}$ is methyl, $R_5$ is 4-fluorophenyl, $R_{54}$ is hydrogen, $X_1$ is =CH—, k is one and n is zero).

Refer to Chart G.

The mesylate reaction mixture of Example 12 is prepared on the same scale and cooled to 0° for one hour and then warmed to room temperature for one hour. An additional 1.5 gms of triethylamine is added and then a solution of 2.43 gms of m-phenylpiperazine and 10 ml of methylene chloride. The solution is heated to reflux for eighteen hours. The reaction mixture is then cooled and quenched with cold aqueous sodium hydroxide. The mixture is then extracted with methylene chloride, dried over sodium sulfate, and concentrated in vacuo to yield 5.2 gms of yellow oil. This oil is then chromatographed over silica gel by eluting with methanol chloroform solvent sysem used and 20 ml fractions taken. Fractions 31-65 yield a product having a weight of 2.3 gms. This oil is then crystallized from a tetrahydrofuran hexane mixture yielding 0.93 gms of the titled product having a melting point of 109°-110° C. The Carbon:Hydrogen:Nitrogen ratio is 72.66:7.18:15.20.

Infrared absorptions are observed at 3050, 2780, 1685, 1605, 1580, 1515, 1225, 860, 805, 760 and 690. NMR absorptions are observed at 2.0, 3.2, 2.8, 6.9 and 7.3 $\delta$. The mass spectrum exhibits peaks at m/e 233, 232, 203, 190, 175, 161, 145, 132, 104 and 70.

EXAMPLE 14

1-(4-Flourophenyl)-5-methyl-N-(2-phenylethyl)-1H-imidazole-2-ethanamine, dihydrochloride (Formula LXIII of Chart G: $R_1$ is $\beta$-phenethylamino, $R_{34}$ is methyl, $R_5$ is 4-fluorophenyl, $R_{54}$ is hydrogen, $X_1$ is =CH=, k is one and n is zero).

Refer to Chart G.

The mesylate mixture described in Example 12 is prepared from 2.46 g of the alcohol in 10 ml of methylene chloride and 1.3 gms of triethylamine in 10 ml of methylene chloride and 1.4 gms of methanesulfonyl chloride in 10 ml of methylene chloride. The reaction mixture is allowed to stir at 0° C. for one hour and then at room temperature for one hour. An additional 1.3 gms of triethylamine is added and 1.5 gms of $\beta$-phenethylamine are added and the resulting mixture heated to reflux under a nitrogen atmosphere for sixteen hours. The resulting mixture is quenched with sodium hydroxide, extracted with methylene chloride and dried over sodium sulfate. It is then concentrated in vacuo to yield an oil. This oil is chromatographed over silica gel using a methanol chloroform solvent system and 20 ml fractions collected. Fractions 40-90 are combined to yield 1.5 gms of an oil. This oil is treated with ethereal hydrochloric acid and the precipitate crystallized from an ethanol diethylether solvent system, filtered, and washed with diethylether to yield 1.28 gms of the titled crystals having a melting point of 211°-214° C. The Carbon:Hydrogen:Nitrogen ratio is 60.46:6.12:10.61.

Infrared absorptions are observed at 3650, 3450, 2710, 2620, 2590, 1625, 1600, 1580, 1550, 1515, 1225, 1155, 845, 820, 750 and 700. NMR absorptions are observed at 2.04, 3-4.5, 7.3 and 7.6, 7.8. The mass spectrum peaks are observed at m/e 233, 232, 203, 202, 201, 191, 190, 189, 105 and 95.

EXAMPLE 15

1-(4-Chlorophenyl)-4-[2-(5-methyl-1-phenyl-1H-imidazol-2-yl)ethyl]piperazine (Formula LXXIII of Chart G: $R_1$ is 4-(4-chlorophenyl)piperazinyl, $R_{34}$ is methyl, $R_5$ is phenyl, $R_{54}$ is hydrogen, $X_1$ is =CH-; k is one and n is zero).

Refer to Chart G.

The mesylate described in Example 1, Part C is prepared from 2.54 gms of the alcohol, and the reaction mixture is stirred at 0° C. for one hour and then at room temperature for one hour. An additional 1.5 gms of triethylamine in 20 ml of methylene chloride and a solution of 2.1 gms of 1-(4-chlorophenyl)piperazine in 40 ml of benzene is added. The mixture is heated to reflux under nitrogen atmosphere for eighteen hours.

The solution is then quenched with cold aqueous sodium hydroxide, separated, and dried over sodium sulfate. It is then concentrated in vacuo 45° C. to yield a yellow oil having a weight of 6 gms. This oil is then chromatographed over silica gel using a methanol chloroform solvent system and 20 ml fractions taken. Fractions 54–90 are combined to yield 1.32 gms of product. This product is then crystallized from an ethyl acetate-hexane solvent system, washed with hexane, to yield 1.10 gms of crystals having a melting point of 136°–137° C. The Carbon:Hydrogen:Nitrogen ratio is 69.67:6.84:14.64.

Infrared absorptions are observed at 3100, 3060, 2780, 1625, 1600, 1585, 1570, 1495, 1415, 1245, 1150, 1000, 830, 810 and 700. NMR absorptions are observed at 2.0, 2.5, 2.74, 6.8, 7.2 and 7.5 δ. The mass spectrum exhibits peaks at m/e 228, 215, 214, 209, 195, 186, 185, 172, 171 and 70.

EXAMPLE 16

1-(4-Chlorophenyl)-4-[2-(5-methyl-4-phenyl-4H-1,2,4-triazol-3-yl)ethyl]piperazine, dihydrochloride, dihydrate (Formula LXXIII of Chart G: $R_1$ is 4-(4-chlorophenyl)piperizinyl, $R_{34}$ is methyl, $R_5$ is phenyl, $R_{54}$ is hydrogen, $X_1$ is —N=, k is one and n is zero).

Refer to Chart G.

The mesylate described in Example 1, Part C, is prepared from 2.5 gms of the alcohol and the resulting mixture is allowed to stir for one hour to 0° C. and then at room temperature for one hour. To this mixture is added 1.6 gms of triethylamine in 10 ml of methylene chloride and 3.47 gms of 1-(4-chlorophenyl)piperazine. The mixture is heated to reflux over three days and is then quenched with cold aqueous sodium hydroxide, separated, and extracted with chloroform, washed with a sodium chloride solution and dried over sodium sulfate. It is then concentrated in vacuo to yield a solid residue having a weight of 6.2 gms. The solid is then chromatographed over silica gel using a methanol chloroform solvent system and 20 ml fractions taken. Fractions 41–100 are combined to yield 3.5 gms of product. This product is then crystallized from a warm ethylacetate solution and treated with ethereal hydrochloric acid to yield the hydrochloride salt which is recrystallized from methanol ether solvent system to yield 1.18 gms of the titled crystals having a melting point of 179°–181° C. The Carbon:Hydrogen:Nitrogen ratio is 51.55:5.57:14.35.

Infrared absorptions are observed at 3480, 3420, 3270, 3060, 2680, 2560, 2460, 1835, 1645, 1595, 1585, 1560, 1500, 825 and 690. NMR absorptions are observed at 2.43, 3.4, 7.0, 7.3 and 7.78 δ. The mass spectrum exhibits peaks at m/e 215, 196, 186, 185, 179, 156, 154, 138, 118 and 77.

EXAMPLE 17

1-(4-Fluorophenyl)-4-[3-[4-(4-fluorophenyl)-4H-1,2,4-triazol-3-yl]propyl]piperazine (Formula LXXXIII of Chart H): $R_1$ is N-(4-fluorophenyl)piperazinyl, $R_5$ is 4-fluorophenyl, $R_{44}$ is hydrogen, $R_{54}$ is hydrogen, m is two and n is zero).

Refer to Chart H.

Following the procedure in Example 6, but employing 4-fluorophenyl isocyanate in place of phenyl isocyanate, 4-hydroxypropyl-4-(4-fluorophenyl)-5-mercapto-4H-1,2,4-triazole (Formula LXXII of Chart H) is prepared having a melting point of 197° C. and a Carbon:Hydrogen:Nitrogen ratio of 52.16:4.78:16.59. 4-(5-fluorophenyl-4H-1,2,4-triazine-3-propanol, having a melting point of 141°–143° C. and a Carbon:Hydrogen:Nitrogen ratio of 59.72:5.47:18.99, is then prepared and converted to the mesylate using the procedure of Example 7, outlined in Chart H. The mesylate is taken up in tetrahydrofuran and treated with 2 equivalents of potassium iodide, followed by an appropriate amount of N-(4-fluorophenyl)piperazine. The mixture is heated to reflux for eighteen hours. The mixture is then extracted with methylene chloride, dried over sodium sulfate, and concentrated in vacuo to yield an oil, which is then chromatographed over silica gel using a methanol chloroform solvent system. Fractions 70–130 are combined and the product is crystallized from a ethyl acetate-hexane solvent system to yield the titled colorless plates having a melting point of 114.5°–115° C. The Carbon:Hydrogen:Nitrogen ratio is 65.78:6.55:17.94.

Infrared absorptions are observed at 3140, 3060, 2800, 1670, 1605, 1525, 1510, 1235, 1215, 1180, 1165, 1145, 850 and 815. NMR absorptions are observed at 2.0, 2.4–2.6, 2.76, 3.05, 6.9–7.3 and 8.28 δ. The mass spectrum exhibits peaks at m/e 234, 233, 207, 204, 179, 177, 176, 122, 84 and 70.

EXAMPLE 18

1-[3-[4-(4-Fluorophenyl)-4H-1,2,4-triazol-3-yl]propyl]-4-phenylpiperazine, dihydrochloride (Formula LXXXIII of Chart H: $R_1$ is 4-phenylpiperazinyl, $R_{44}$ is hydrogen, $R_5$ is 4-fluorophenyl, $R_{54}$ is hydrogen, $X_1$ is —N—, m is 2 and n is zero).

Refer to Chart H.

The mesylate described in Example 17 is prepared from 2.13 gms of the alcohol and reacted with two equivalents of N-phenylpiperazine in 10 ml of methylene chloride, and the solution is refluxed overnight. The reaction mixture is extracted with methylene chloride, dried over sodium sulfate, and concentrated in vacuo to yield 6.23 gms of an oil. This solution is chromatographed over silica gel using a methanol-chloroform solvent system, collecting 20 ml portions. Fractions 70–130 are combined, yielding an oil of 2.3 gms. This oil is then treated with ethereal HCl and allowed to crystallize. It is recrystallized from a methanol diethyl ether solvent system to give 1.9 gms of the titled white crystals having a melting point of 232°–236° C. The Carbon:Hydrogen:Nitrogen ratio is 57.52:6.18:15.90.

Infrared absorptions are observed at 3480, 3420, 2440, 1635, 1600, 1545, 1515, 1495, 1235, 1220, 955, 940, 845 and 780. NMR absorptions are observed at 2.28, 3.0, 3.2, 3.2–3.8, 5.8, 6.8–7.3, 7.5–7.9 and 9.6. The mass spectrum exhibits peaks at m/e 333, 331, 296, 288, 255, 179, 139, 124 and 111.

EXAMPLE 19

N-methyl-4-phenyl-N-(2-phenylethyl)-4H-1,2,4-triazole-3-propanamine, dihydrochloride (Formula LXXXIII of Chart H: $R_1$ is N-methylphenethylamino, $R_{44}$ is hydrogen, $R_5$ is phenyl, $R_{54}$ is hydrogen, $X_1$ is —N—, m is 2 and n is zero).

Refer to Chart H.

The mesylate described in Example 6 is prepared from 4.23 gms of the alcohol and the mixture is stirred for one hour. Then a solution of 6.2 gms of N-methyl-δ-phenylethylamine in 200 ml of methylene chloride is added at room temperature. The solution is heated to reflux for eighteen hours and then cooled. The mixture is then quenched with cold aqueous sodium hydroxide solution separated, washed with a sodium chloride solution, and dried over sodium sulfate and subsequently concentrated in vacuo to yield a yellow oil having a weight of 10.42 gms. This oil is then chromatographed over silica gel using methanol chloroform solvent system and 20 ml fractions are collected. Fractions 24–48 are combined to yield the product having a weight of 2.3 gms. The hydrochloride salt was then prepared from a methanol, acetone solvent system and the precipitate filtered and dried to yield the titled powder having a weight of 1.52 gms and a melting point of 174°–177° C. The Carbon:Hydrogen:Nitrogen ratio is 61.46:6.78:14.31.

Infrared absorptions are observed at 3100, 3060, 2420, 1835, 1600, 1540, 1495, 960, 770, 750 and 695. NMR absorptions are observed at 2.24, 2.8, 2.8–3.4, 7.3, 7.7 and 9.6$\delta$. The mass spectrum exhibits peaks at m/e 230, 229, 187, 186, 162, 159, 158, 105, 84 and 36.

EXAMPLE 20

1-(4-Chlorophenyl)-4-[3-[4-(4-fluorophenyl)-4H-1,2,4-triazol-3-yl]propyl]piperazine, dihydrochloride (formula LXXXIII of Chart H: $R_1$ is 4-(4-chlorophenyl)-piperizinyl, $R_{44}$ is hydrogen, $R_5$ is 4-fluorophenyl, $R_{54}$ is hydrogen, $X_1$ is -N-, m is 2 and n is zero).

Refer to Chart H.

The mesylate described in Example 17 is prepared from 4.4 gms of the alcohol and is dissolved in 40 ml of methylene chloride 2.8 gms of triethylamine is added followed by 4.18 gms of N-(4-chlorophenyl)piperazine in 10 ml of methylene chloride. The solution is then heated to reflux for eighteen hours, cooled and quenched with cold aqueous sodium hydroxide, separated, and washed with sodium chloride and dried over sodium sulfate and concentrated in vacuo to yield 9 gms of an oil. This is chromatographed over silica gel using a methanol chloroform solvent system and yielding 5 gms of product as an oil. This oil is then treated with a etheral hydrochloric acid and the precipitate recrystallized from methanol ether solvent system yielding 1.7 gms of the titled crystals having a melting point of 165°–170° C. The Carbon:Hydrogen:Nitrogen ratio is 53.20:6.25:14.94.

Infrared absorptions are observed at NMR absorptions are observed at 2.2–2.3, 3.0–3.2, 3.0–3.8, 6.8, 7.0–7.3, 7.6–7.8, and 9.8 $\delta$. The mass spectrum exhibits peaks at m/e 259, 234, 233, 204, 195, 190, 177, 176, 84 and 36.

EXAMPLE 21

1-[3-[4-(4-Fluorophenyl)-4H-1,2,4-triazol-3-yl]propyl]-4-(4-methoxyphenyl)piperazine (Formula LXXXIII of Chart H: $R_1$ is 4-(4-methoxyphenyl)piperazinyl, $R_{44}$ is hydrogen, $R_5$ is 4-fluorophenyl, $R_{54}$ is hydrogen, $X_1$ is —N—, m is 2 and n is zero).

Refer to Chart H.

4.6 gms of the mesylate described in Example 17 is prepared from 3.62 gms of the alcohol and this mesylate is then dissolved in 40 ml of tetrahydrofuran. 4.15 gms of potassium iodide and 4.0 gms of triethylamine are added. To this mixture is added 4.78 gms of 1(4-methoxyphenyl)piperazine. The mixture is heated to reflux for six hours, then quenched with aqueous soidum hydroxide, extracted with chloroform, washed with sodium chloride solution dried over sodium sulfate and concentrated in vacuo to yield 6.8 gms of an oil. This oil is then chromatographed over silica gel, using a methanol chloroform solvent system and 20 ml fractions taken. Fractions 24–28 are combined to yield 2.5 gms of product. This is then crystallized from an ethylacetate hexane mixture to yield 1.68 gms of the titled product having a melting point of 96°–97° C. The Carbon:Hydrogen:Nitrogen ratio is 66.64:6.53:17.50.

Infrared absorptions are observed at 3140, 2760, 1665, 1605, 1515, 1245, 1235, 1175, 855 and 820. NMR absorptions are observed at 1.9, 2.4, 2.75, 2.5, 6.85, 7.2–7.3, and 8.17 $\delta$. The mass spectrum exhibits peaks at m/e 234, 233, 204, 191, 177, 176, 163, 162, 135, and 120.

EXAMPLE 22

1-(4-Chlorophenyl)-4-[3-(4-phenyl-4H-1,2,4-triazol-3-yl)propyl]piperazine (Formula LXXXIII of Chart H: $R_1$ is 4-(4-chlorophenyl)piperazinyl, $R_{44}$ is hydrogen, $R_5$ is phenyl, $R_{54}$ is hydrogen, $X_1$ —N—, m is 2 and n is zero).

Refer to Chart H.

5.51 gms of the mesylate described in Example 19 are prepared and combined with 5.44 gms of 1(4-chlorophenyl)piperazine, 4.6 gms of potassium iodide, 3.0 gms of triethylamine, and 50 ml of tetrahydrofuran. This mixture is then heated to reflux for six hours and allowed to stir at room temperature for two days. The resulting mixture is then quenched with sodium hydroxide and concentrated in vacuo, extracted with chloroform, washed with sodium chloride, dried over sodium sulfate and the remainder concentrated in vacuo at 45° C. to yield 9.1 gms of an oil. This oil is chromatographed over silica gel using a methanol chloroform solvent system and 20 ml fractions taken. Fractions 25–48 are combined to yield 4.23 gm of a white solid. This is then crystallized from ethyl acetate, filtered and recrystallized again from ethyl acetate to yield 3.28 gms of the titled product having a melting point of 144°–146° C. The Carbon:Hydrogen:Nitrogen ratio is 66.11:6.28:18.36.

Infrared absorptions are observed at 3100, 2780, 1735, 1600, 1590, 1570, 1520, 1505, 1240, 1170, 805, 765, and 695. NMR absorptions are observed at 1.948, 2.4, 2.4–3.1, 2.8, 6.8–7.2, 7.3, 7.5 and 8.2 $\delta$. The mass spectrum exhibits peaks at m/e 241, 223, 216, 215, 195, 186, 172, 159, 158 and 138.

EXAMPLE 23

1-(2-Chlorophenyl)-4-[3-(4-phenyl-4H-1,2,4-triazol-3-yl)propyl]piperazine, dihydrochloride (Formula LXXXIII of Chart H: $R_1$ is 4-(2-chlorophenyl)piperazinyl, $R_{44}$ is hydrogen, $R_5$ is phenyl, $R_{54}$ is hydrogen, $X_1$ is —N—, m is 2 and n is zero).

Refer to Chart H.

5.51 gms of the mesylate described in Example 19, is prepared and dissolved in 33 ml of tetrahydrofuran. To this solution 4.5 gms of potassium iodide, 3.0 gms of triethylamine, and 4.96 gms of 1-(2-chlorophenyl)piperazine in 50 ml of tetrahydrofuran are added. 40 additional milliliters of tetrahydrofuran is added and the mixture heated to reflux for six hours. The mixture is then quenched with aqueous sodium hydroxide, extracted with chloroform, washed with saturated sodium chloride, dried over sodium sulfate and concentrated in vacuo at 45° C. to yield 10.33 gms of product. This is then chromatographed over silica gel using a methanol chloroform solvent system and 20 ml fractions taken. Fractions 24–70 are combined to yield 5.1 gms of an oil. This oil is then treated with ethereal hydrochloric acid and the salt crystallized from methanol acetone ether solvent and filtered to yield 4.35 gms of the titled product having a melting point of 228°–232° C. The Carbon:Hydrogen:Nitrogen ratio is 55.25:5.73:15.30.

Infrared absorptions are observed at 3100, 2780, 1735, 1600, 1590, 1570, 1520, 1505, 1240, 1170, 805, 765, and 695. NMR absorptions are observed at 3.0, 3.0–3.6, 3.4, 2.3, 7.2–7.5, 7.7 and 9.8 $\delta$.

EXAMPLE 24

1-(3-Chlorophenyl)-4-[3-(4-phenyl-4H-1,2,4-triazol-3-yl)propyl]piperazine (Formula LXXXIII of Chart H: $R_1$ is 4-(3-chlorophenyl)piperazinyl, $R_{44}$ is hydrogen, $R_5$ is phenyl, $R_{54}$ is hydrogen, $X_1$ is —N—, m is 2 and n is zero).

Refer to Chart H.

5.5 gms of the mesylate described in Example 19 are prepared and dissolved in 33 ml of tetrahydrofuran. To this are added 4.6 gms of potassium iodide, 3.0 gms. of 1-(3-chlorophenyl)piperazine in 5.26 gms of 3-chloropiperazine and 50 ml of tetrahydrofuran. To this mixture is added an additional 30 ml of tetrahydrofuran. The reaction mixture is refluxed for six hours and allowed to cool. It is then quenched with sodium hydroxide, concentrated in vacuo, extracted with chloroform, washed with saturated sodium chloride, dried over sodium sulfate, and concentrated in vacuo to yield 8.82 gms of oil. This is then chromatographed over silica gel using a methanol chloroform solvent system and 20 ml fractions are taken. Fractions 24–48 are combined to yield 5.8 gms of product. It is then recrystallized from an ethyl acetate hexane solvent system yielding 3.44 gms of the titled product having a melting point of 95°–97° C. The Carbon:Hydrogen:Nitrogen ratio is 66.14:6.28:18.36.

Infrared absorptions are observed at 3100, 2800, 2780, 1725, 1600, 1565, 1520, 1505, 1490, 1250, 1245, 1170, 1145, 990, 970, 775, 760, 695 and 675. NMR absorptions are observed at 1.94, 3.4, 2.8, 2.4, 3.1, 6.8, 7.3, 7.6 and 8.2 $\delta$. The mass spectrum exhibits peaks at m/e 241, 223, 216, 215, 195, 186, 172, 159, 158, and 70.

EXAMPLE 25

1-(4-Methoxyphenyl)-4-[3-(4-phenyl-4H-1,2,4-triazol-3-yl)propyl]piperazine (Formula LXXXIII of Chart H: $R_1$ is 4-(4-methoxyphenyl)piperazinyl, $R_{44}$ is hydrogen, $R_5$ is phenyl, $R_{54}$ is hydrogen, $X_1$ is —N—, m is 2 and n is zero).

Refer to Chart H.

The mesylate described in Example 19 is prepared from 3.60 gms of alcohol and is dissolved in tetrahydrofuran. To this solution is added 4.71 gms of 1(4-methoxyphenyl)piperazine, and 4.05 gms of potassium iodide in tetrahydrofuran. The mixture is then heated to reflux for twelve hours. The mixture is cooled, quenched with cold aqueous sodium hydroxide solution, extracted with chloroform, washed with saturated sodium chloride and dried over sodium sulfate. This solution is then concentrated in vacuo to yield an oil having a weight of approximately 7.6 gms. This oil is chromatographed over silica gel using a methanol chloroform solvent system and 20 ml fractions taken. Fractions 20–56 are combined to yield a product having a weight of 3.8 gms. It is recrystallized from warm ethyl acetate-hexane solvent system, filtered and washed, again with ethyl acetate-hexane solvent system to yield 3.4 gms of the titled beige needles, having a melting point of 142°–144° C. The Carbon:Hydrogen:Nitrogen ratio is 69.87:7.11:18.75.

Infrared absorptions are observed at 3120, 27600, 1670, 1615, 1600, 1590, 1515, 1255, 1235, 1180, 1135, 1040, 1030, 825 and 695. NMR absorptions are observed at 1.92, 2.34, 2.5, 3.0, 2.8, 3.76, 6.8, 7.3, 7.5 and 8.2 $\delta$. The mass spectrum exhibits peaks at m/e 216, 215, 191, 186, 163, 162, 159, 158, 135 and 120.

EXAMPLE 26

1-(2-Methylphenyl)-4-[3-(4-phenyl-4H-1,2,4-triazol-3-yl)propyl]piperazine, dihydrochloride (Formula LXXXIII of Chart H: $R_1$ is 4-(2-methylphenyl)piperazinyl, $R_{44}$ is hydrogen, $R_5$ is phenyl, $R_{54}$ is hydrogen, $X_1$ is —N—, m is 2 and n is zero).

Refer to Chart H.

4.9 gms of the mesylate described in Example 19 is prepared and then added to a solution containing 1-(o-tolyl)piperazine, 4.66 gms, and 2.6 gms of triethylamine, and 2.65 gms of potassium iodide in 125 ml of tetrahydrofuran. This is allowed to react at room temperature for one hour. The mixture is then heated to reflux under a nitrogen atmosphere for eighteen hours. It is then cooled and quenched with cold aqueous sodium hydroxide. The tetrahydrofuran is removed in vacuo at 40° C. The remainder is then extracted with chloroform, washed with a saturated solution of sodium chloride, dried over sodium sulfate and concentrated in vacuo at 40° C. to yield a brown oil having a weight of 8 gms. This brown oil is then chromatographed on silica gel using methanol and chloroform as a solvent system. 20 ml fractions are then collected. Fractions 16–48 are combined to yield a product having a weight of 4.3 gms. This is then crystallized from a warm ethylacetate hexane solvent system which is then treated with ethereal hydrochloric acid and recrystallized from a methanol/ether solvent system yielding 0.4 gms of the titled salt having a melting point of 204°–208° C. The Carbon:Hydrogen:Nitrogen ratio is 61.26:6.83:16.16.

Infrared absorptions are observed at 3460, 2560, 2180, 1635, 1615, 1595, 1590, 1575, 1540, 1500, 1495, 1340, 1210, 975, 950, 770, 760 and 695. NMR absorptions are observed at 2.38, 3.0–3.6, 3.28, 7.0–7.3, 7.8 and 9.9 $\delta$. The mass spectrum exhibits peaks at m/e 216, 215, 203, 186, 175, 159, 158, 146, 118 and 36.

EXAMPLE 27

1-(2-Methoxyphenyl)-4-[3-(4-phenyl-4H-1,2,4-triazol-3-yl)propyl]piperazine, trihydrochloride methanol hemi solvent (Formula LXXXIII of Chart H: $R_1$ is. 4-(2-methoxyphehyl)piperazinyl, $R_{44}$ is hydrogen, $R_5$ is phenyl, $R_{54}$ is hydrogen, $X_1$ is —N—, m is 2 and n is zero).

Refer to Chart H.

The mesylate described in Example 19 is prepared from 3.16 gms of the alcohol and is then treated with the 4.9 gms of 1-(2-methoxyphenyl)piperazine in the manner described in Example 22 to yield 7.9 gms of crude product. This is then chromatographed over silica gel using methanol and chloroform as the solvent system and 20 ml fractions are collected. Fractions 16–32 are combined to yield 2.25 gms of product. It is then treated with etheral hydrochloric acid and precipitated from methanol ether solvent system to yield 1.7 gms of crystalline product having a melting point of 215°–218° C. This product is then recrystallized from warm ethyl acetate/hexane solvent system, filtered and washed with ethyl acetate/hexane solvent system, yielding the titled beige needles weighing 3.4 gms and having a melting point of 215°–218° C. The Carbon:Hydrogen:Nitrogen ratio is 52.93:6.14:13.75.

Infrared absorptions are observed at 3440, 3400, 2640, 2520, 2400, 1635, 1610, 1600, 1545, 1515, 1495, 1490, 1480, 1275, 1260, 1020, 955, 770, 760 and 690. NMR absorptions are observed at 2.38, 3.0, 3.1–3.6, 3.88, 7.08, 7.78 and 9.88 $\delta$. The mass spectrum exhibits peaks at m/e 228, 219, 216, 215, 191, 186, 159, 158, 38 and 36.

EXAMPLE 28

$\alpha$-[[[2-(3,4-dichlorophenyl)ethyl]methylamino]methyl]-5-methyl-4-phenyl-4H-1,2,4-triazole-3-methanol (Formula XXXV of Chart C, $R_{34}$ is methyl, $R_5$ is phenyl, and $R_1$ is ((2-(3,4-dichlorophenyl)ethyl)methylamino)methyl), and n is zero).

Refer to Chart C.

4.77 g of 1-methylphenyltriazole, 9.0 g of paraformaldehyde and 240 ml of xylene are mixed and heated to 125° C. for 4 hr. The solution is filtered and concentrated in vacuo to yield 5-methyl-4-phenyl-4H-1,2,4-triazole-3-methanol, a compound of Formula XXXII of Chart C. This product is chromatographed on silica gel and eluted with 2 l of 7% methanol/chloroform.

0.86 g of the product of the preceeding paragraph is treated with 9 g (0.04 mole) of maganese oxide in 100 ml of chloroform. The mixture is stirred for 3 hr at room temperature, filtered, and concentrated in vacuo to yield 0.62 g of a white solid which is 5-methyl-4-phenyl-4H-1,2,4-triazole-3-carboxaldehyde, a compound of the Formula XXXIII of Chart C.

0.25 g of the aldehyde of the preceeding paragraph is dissolved in 25 ml of methanol at 10°–15° C. and is added in small portions to an equivalent amount of diazomethane. The progress of the reaction is followed by thin layer chromatography. At the completion of the reaction, dry ice is added and the mixture is concentrated in vacuo to yield a semi-solid residue, which contains a mixture of 3-methyl-5-(2-oxiranyl)-4-phenyl-4H-1,2,4-triazole, a compound of Formula XXXIV of Chart C, the corresponding methyl ketone, and other impurities. The epoxide is separated on a Michael-Miller column packed with silica gel and eluted with 3% methanol/chloroform to yield 0.67 g of solid crystals of melting point 141°–142° C.

The epoxide from the previous paragraph (0.42 g, 0.002 mole) is mixed with 0.82 g (0.004 mole) of $\beta$-(3,4-dichlorophenyl)-ethyl-N-methylamine in 4 ml of tetrahydrofuran. This mixture is stirred at room temperature for 20 hr. The solvent is evaporated under nitrogen and the resulting oil is chromatographed on a Michel-Miller column packed with silica gel and eluted with 3% methyl/chloroform. The product is recrystallized from ether to yield 0.4 g of the titled colorless crystals, having a melting point of 110.5°–111° C. The Carbon:Hydrogen:Nitrogen:Chlorine ratio is 58.96:5.5:13.48:17.50.

EXAMPLE 29

1-[3-[5-(methylthio)-4-phenyl-4H-1,2,4-triazole-3-yl]-propyl]-4-phenyl-piperazine, dihydrochloride, hemi hydrate (Formula LXXXIII of Chart H, $R_{44}$ is methylthio, $R_5$ is phenyl, $R_{54}$ is hydrogen, $R_1$ is piperazino, n is zero and m is 3)

Following the procedure of Example 6 a triazolomesylate corresponding to the titled product is prepared and reacted with n-phenylpiperazine and potassiumiodide to yield the titled product having a melting point of 190°–192° C. The Carbon:Hydrogen:Nitrogen:Chloride:Sulfur ratio is 55.25:6.29:14.61:15.93:6.88.

EXAMPLE 30

N-[2-(4-chlorophenyl)-ethyl]-N-methyl-4-phenyl-4H-1,2,4-triazole-3-propanamine, dihydrochloride (Formula LXXIII of Chart H, $R_{44}$ is hydrogen, $R_5$ is phenyl, $R_{54}$ is hydrogen, $R_1$ is N-methyl-parachlorophenylethylamino, n is zero, m is 2)

Refer to Chart H.

Following the procedure of Example 1, and using the appropriate alcohol, the titled crystals are obtained having a melting point of 172°–175° C. The Carbon:Hydrogen:Nitrogen:Chlorine ratio is 56.08:5.94:13.10:16.35.

EXAMPLE 31

1-(phenylmethyl)-4-[3-(4-phenyl-4H-1,2,4-triazol-3-yl)propyl]piperizine, dihydrochloride (Formula LXXXIII of Chart H: $R_{44}$ is hydrogen, $R_5$ is phenyl, $R_{54}$ is hydrogen, $R_1$ is 4-benzylpiperazino, n is zero and m is 2)

Refer to Chart H.

Following the procedure of the preceeding example, and starting with the appropriate alcohol, the titled product is obtained and converted to its HCl salt having a melting point of 231°–233° C. The Carbon:Hydrogen:Nitrogen:Chlorine ratio is 60.52:6.75:16.33:16.33.

EXAMPLE 32

4-(phenylmethyl)-1-[3-(4-phenyl-4H-1,2,4-triazol-3-yl)propyl]-piperidine, (Z)-2-butanedioate (1:1) (formula LXXXIII of Chart H: $R_{44}$ is hydrogen, $R_5$ is phenyl, $R_1$ is (4-phenylmethyl)piperidinyl, $R_{54}$ is hydrogen, m is two and n is zero).

Refer to Chart H.

Using the procedure of Example 6, and starting with the appropriate alcohol, the titled product is obtained as an oil and converted to its salt having a melting point of 99°–102° C. The Carbon:Hydrogen:Nitrogen ratio is 67.3:6.77:11.56.

EXAMPLE 33

1-(Diphenylmethyl)-4-[3-(4-phenyl-4H-1,2,4-triazol-3-yl)propyl]-piperazine, trihydrochloride (Formula LXXXIII of Chart H, $R_5$ is phenyl, $R_1$ is diphenylmethyl piperazino, $R_{54}$ is hydrogen, $R_{44}$ is hydrogen, n is zero and m is 2)

Refer to Chart H.

Following the procedure of the preceeding example, and starting from the appropriate alcohol, the titled product is obtained and crystalized as an HCl salt, having a melting point of 248°–249° C. The Carbon:Hydrogen:Nitrogen:Chlorine ratio is 61.10:6.23:12.88:19.07.

EXAMPLE 34

N-[2-(3,4-dichlorophenyl)-ethyl]-N-methyl-4-phenyl-4H-1,2,4-triazol-3-propanamine, bis(4-methylbenzenesulfonate) (Formula LXXXII of Chart H, $R_5$ is phenyl, $R_1$ is N-(2-(3,4-dichlorophenyl)-ethyl)-propanamino, $R_{44}$ is hydrogen, $R_{54}$ is hydrogen, n is zero and m is one)

Refer to Chart H.

Following the procedure of the preceeding example, and starting with the appropriate alcohol, the titled product is obtained and recrystallized as a bis(4-methylbenzenesulfonate)salt having a melting point of 198°-200° C. The Carbon:Hydrogen:Nitrogen:Chlorine:Sulfur ratio is 55.62:5.15:7.49:9.68:8.99.

EXAMPLE 35

α-[[4-(4-chlorophenyl)-1-piperazinyl]methyl]-5-methyl-4-phenyl-4-1,2,4-triazol-3-methanol (Formula XXXV of Chart C, $R_{34}$ is methyl, $R_5$ is phenyl, $R_1$ is 4-chlorophenyl-1-piperazino, and n is zero)

Refer to Chart C.

The appropriate epoxide of the Formula XXXIV of Chart C is prepared as in Example 28. This product is then reacted with N-(p-chlorophenyl)-piperazine to yield the titled product. Upon purification, the crystals had a melting point of 164.5°-166° C. The Carbon:Hydrogen:Nitrogen:Chlorine ratio is 59.69:5.93:16.84:10.67.

EXAMPLE 36

5-[3-[methyl(phenylethyl)amino]propyl]-α-4-diphenyl-4H-1,2,4-triazol-3-methanol (Formula XCVIII of Chart I, $R_{35}$ is phenyl, $R_{13}$ is hydrogen, $R_5$ is phenyl, $R_{16}$ is hydrogen, $R_1$ is methylphenylethylamino, n is zero and m is 2)

Refer to Chart I.

2.10 g (6.55 mmole) of the product of Example 19 is treated with 9.0 ml (14.0 mmole) of n-butyllithium in hexane (1.6 N) in 15 ml of tetrahydrofuran. The flask is chilled under nitrogen in dry ice-isopropanol bath to −75° C. prior to the addition of the n-butyllithium which is added slowly over one min. After the addition is complete the reaction is stirred for 5 min and allowed to warm to −55° to −50° C. Benzaldehyde (6.6 mmole) is added to the solution which is maintained at −78° C. The reaction is allowed to warm to 0° and is quenched with water. The tetrahydrofuran is removed in vacuo and the mixture is diluted with 25 ml of 10% hydrochloric acid, washed with ether and cooled in an ice bath. The solution is made basic with 50% sodium hydroxide solution and extracted with chloroform and then water and saturated sodium chloride solution is added. The mixture is dried over sodium sulfate and concentrated in vacuo to yield a brown oil which is chromatographed on a Michael-Miller HPLC column and eluted with 4% methanol/chloroform to yield the title crystals having a melting point of 144°-146° C. The Carbon:Hydrogen:Nitrogen:Chlorine ratio is 62.34:6.45:10.55:13.30.

EXAMPLE 37

α-[[[2-(4-chlorophenyl)ethyl]methylamino]methyl]-5-methyl-4-phenyl-4H-1,2,4-triazol-3-methanol(Formula XXXV of Chart C, $R_{34}$ is methyl, $R_5$ is phenyl, $R_1$ is 4-chlorophenylethylmethylamino, and n is zero)

Refer to Chart C.

The appropriate epoxide is prepared as in Example 28, and converted to the titled product by the procedure of Chart C. NMR absorptions (CDCl$_3$) for this titled product are observed at: δ6.8-7.7 (9H, muptiplet, aromatic H), 4.45 (1H, doublet of doublets, $J_{AB}$=10 Hz, $J_{BX}$=5.7 Hz, CH-O), 2.5-3.3 (6H, multiplet, N—CH$_2$, benzylic CH$_2$), 2.26 (3H, singlet, CH$_3$-N), and 2.25 (3H, singlet, CH$_3$-C).

EXAMPLE 38

4-phenyl-N-(2-phenyl-ethyl)-4H-1,2,4-triazol 3-propanamine, dihydrochloride (Formula LXXXIII of Chart H, $R_5$ is phenyl, $R_1$ is propanamino, $R_{44}$ is hydrogen, $R_{54}$ is hydrogen, n is zero and m is 2)

Refer to Chart H.

Following the procedure of Example 6, and starting from the appropriate alcohol, the titled product is obtained having a melting point of 201°-205° C.

EXAMPLE 39

α-[[[2-(4-Chlorophenyl)ethyl]methylamino]ethyl]-5-(n-propyl)-4-phenyl-4H-1,2,4-triazole-3-methanol (Formula XLV of Chart D, $R_5$ is phenyl, $R_1$ is [2-(4-chlorophenyl)ethyl]methylamino, $R_{34}$ is n-propyl, $X_1$ is =N—, and n is zero).

Refer to Chart D.

One equivalent of 4-phenyl-5-(1-propyl)-4H-1,2,4-triazole-3-carboxaldehyde of the Formula XLI is treated with one equivalent of vinyl lithium reagent in tetrahydrofuran to yield the corresponding allylic alcohol. The mixture is then treated with an excess of manganese dioxide. To this mixture is added one equivalent of [2-(4-chlorophenyl)ethyl]methylamine. The ketone thus prepared is reduced with sodium borohydride to yield the titled product.

EXAMPLE 40

N-[2-(4-chlorohenyl)ethyl]-3-ethoxy-N-methyl-3-[4-phenyl-5-(n-propyl)-4H-1,2,4-triazol-3-yl]propaneamine (Formula LII of Chart E, $R_{26}$ is ethyl, $R_5$ is phenyl, $R_{34}$ is propyl, $X_1$ is =N—, $R_1$ is [2-(4-chlorophenyl)ethyl]methylamino, m is 2, and n is zero).

Refer to Chart E.

One equivalent of the alcohol prepared in the preceeding Example is dissolved in dimethyl formamide and treated with sodium hydride. The mixture is treated with one equivalent of ethyl bromide, yielding the titled product.

EXAMPLE 41

5-Methylsulfonyl-4-phenyl-4H-1,2,4-triazole-3-methanol (Formula LXIV of Chart F, $R_{17}$ is methyl, $R_5$ is phenyl, n is zero, $R_1$ is [2-(4-chlorophenyl)ethyl]methylamino, $R_{54}$ is hydrogen, and m is zero).

Refer to Chart F. One equivalent of 5-mercapto-4-phenyl-4H-1,2,4-triazole-3-methanol (Formula XXIII of Chart B, $R_{24}$ is hydroxymethyl, $R_5$ is phenyl, n is zero) is prepared according to Chart B. One equivalent of this compound is treated with sodium hydroxide and bromoethane. This product is then oxidized with aqueous hydrogen peroxide to yield 5-methylsulfinyl-4-phenyl-4H-1,2,4-triazole-3-methanol. This product is further oxidized by treating it with m-chlorobenzoic acid at 25° C. for 24 hrs to yield the titled product.

EXAMPLE 42

N-[2-(4-Chlorophenyl)ethyl]-3-ethyl-N-methyl-3-[4-phenyl-5-(n-propyl)-4H-1,2,4-triazol]propanamine (Formula CIV of Chart J, $R_{34}$ is n-propyl, $R_{26}$ is ethyl, $R_5$ is phenyl, $X_1$ is =N—, $R_1$ is [2-(4-chlorophenyl)-ethyl]methylamino, n is zero and m is two).

Refer to Chart J.

One equivalent of the product of Example 39 is oxidized by treating it with dimethylsulfoxide, anhydrous orthophosphoric acid ($H_3PO_4$), and dicyclohexylcarbodiimide. The resulting ketone is treated with one equivalent of methylenetriphenylphosphorane. Finally, the product is hydrogenated to yield the titled compound.

EXAMPLE 43

α,1-diphenyl-4-methyl-2-[1-methyl-2-[(2-phenylethyl)-methylamino]ethyl-1H-imidazole-5-methanol (Formula CXIII of Chart K, $R_5$ is phenyl, $R_{35}$ is phenyl, $R_{13}$ is hydrogen, $R_{16}$ is methyl, $R_{11}$ is methyl, $R_1$ is (2-phenylethyl)methylamino, m is one and n is zero).

Refer to Chart K.

4-methyl-2-[1-methyl-2-[(2-phenylethyl)methylamino]ethyl]-1-phenyl-1H-imidazole-5-methanol is prepared by the method of Chart J. This alcohol is oxidized by dissolving it in dimethylformamide and treating it with manganese dioxide. The aldehyde thus formed is treated with one equivalent of methylenetriphenylphosphornae to yield the titled product.

EXAMPLE 44

α-[[[2-(3,4-dichlorophenyl)ethyl]methylamino]methyl]-5-methyl-4-phenyl-4H-1,2,4-triazole-3-methanol, acetate ester (Formula CXII of Chart L, $R_4$ is methyl, $R_5$ is phenyl, $R_1$ is [2-(3,4-dichlorophenyl)ethyl]methylamino, $R_{21}$ is methyl, m is one, $X_1$ is =N—, and n is zero).

Refer to Chart L.

The product of Example 28 is esterified by dissolving it in pyridine and reacting it with one equivalent of acetyl chloride to yield the titled product.

EXAMPLE 45

5-Mercapto-4-phenyl-α-(4-phenyl-1-piperazinyl)methyl-4H-1,2,4-triazole-3-methanol, acetate ester (Formula CXXXIII of Chart M, $R_5$ is phenyl, $R_{21}$ is methyl, $R_1$ 4-phenyl-1-piperazinyl, m is one and n is zero).

Refer to Chart M.

One equivalent of the alcohol corresponding to the titled product is esterified by treating it with acetyl chloride in pyridine. The compound is selectively hydrolyzed by reacting it with one equivalent of sodium bicarbonate to yield the titled compound.

EXAMPLE 46

Following the procedures of the preceeding Examples and the processes depicted in Charts A–M, all of the remaining compounds within the scope of this application are synthetized. Representative examples are:

3[1-methoxy-2-(4-phenyl-1-piperazinyl)ethyl]-4-(phenylmethyl)-4H-1,2,4-triazole-5-methanol, 1-[3-[5-(methoxymethyl)-4-phenyl-4H-1,2,4-triazol-3-yl]propyl]-3-methyl-4-phenylpiperazine, 1-(4-fluorophenyl)-$α^2$-[[methyl(2-phenylethyl)amino]methyl]-$α^5$-phenyl-1H-imidazoledimethanol, 5-(1-cyclohexenyl)-α-[2-(2-phenylethylamino)ethyl]-4-(α,α,α-trifluoro-o-tolyl)-4H-1,2,4-triazole-3-methanol, 4-(3-chlorophenyl)-1-[2-methyl-2-[5-methylsulfinyl-1-[4-(n-propyl)phenyl]-1H-imidazol-2-yl]ethyl]piperazine, 1-[2-[4-[2-(4-chlorophenyl)ethyl]-5-phenylsulfonyl-4H-1,2,4-triazol-3-yl]-2-ethyl]ethyl-4-phenylpiperazine, 5-methyl-4-(4-pyridinyl)-α-[[4-phenyl-2-(phenylmethyl)-1-piperazinyl]propyl]-4H-1,2,4-triazole-3-methanol, 1-[4-[5-(ethoxymethyl)-4-phenyl-4H-1,2,4-triazol-3-yl]-4-methoxybutyl]-3-phenylpiperidine, α-[[4-(4-chlorophenyl)-1-piperazinyl]methyl]-5-methyl-4-(phenylmethyl)-4H-1,2,4-triazole-3-methanol, 5-methyl-4-(phenylmethyl)-α-[2-(4-phenyl-1-piperazinyl)ethyl]-4H-1,2,4-triazole-3-methanol, propionate ester, 1-[α-ethyl-α-[4-(3,4-difluorophenyl)-5-(1-hydroxycyclohexyl)-4H-1,2,4-triazol-3-yl]methyl]-4-(phenylmethyl)piperidine, N,5-dimethyl-1-[4-fluoro-3-(trifluoromethyl)phenyl]-N-(2-phenylethyl)-1H-imidazole-2-methanamine.

FORMULAS

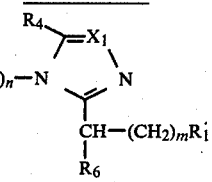

I

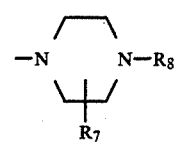

II

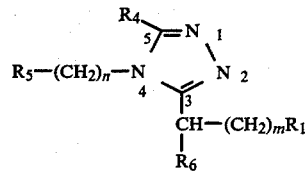

V

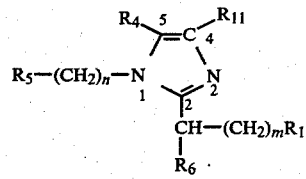

VI

CHART A

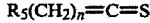

XI

-continued
CHART A
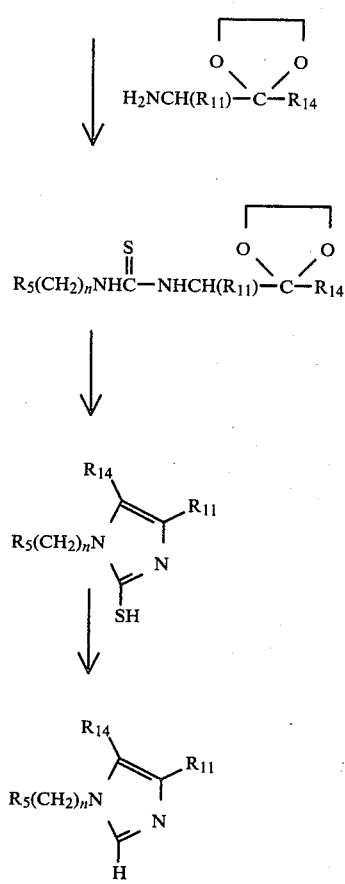
CHART B
R₅(CH₂)ₙN=C=S    XXI
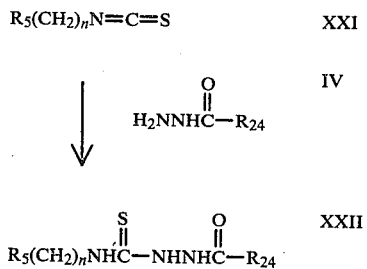
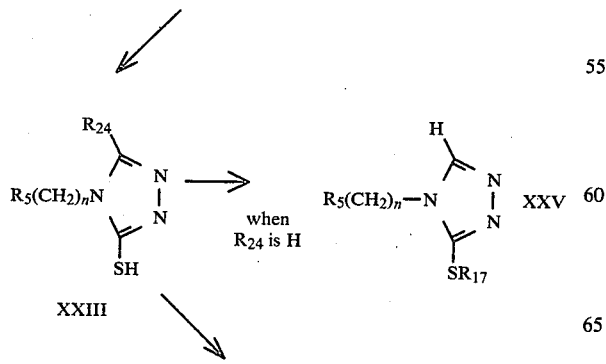
-continued
CHART B
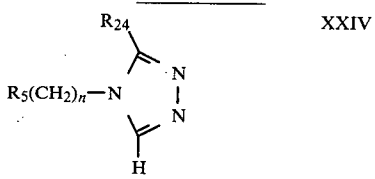
XXIV
CHART C
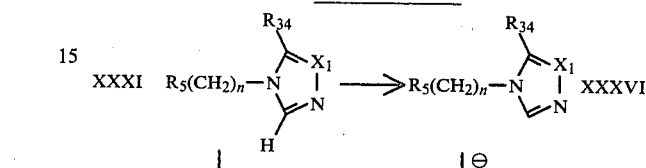
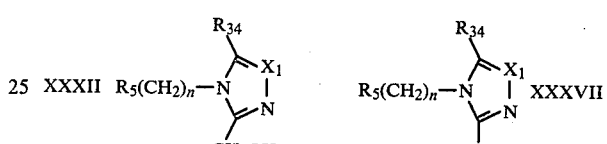
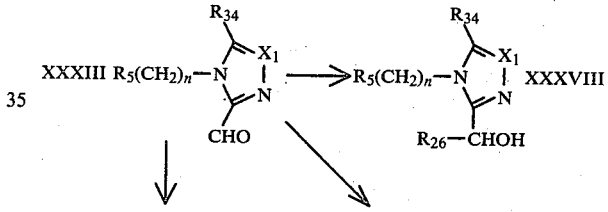
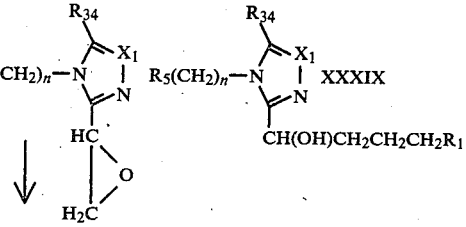
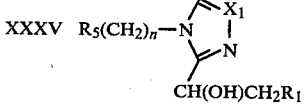
CHART D
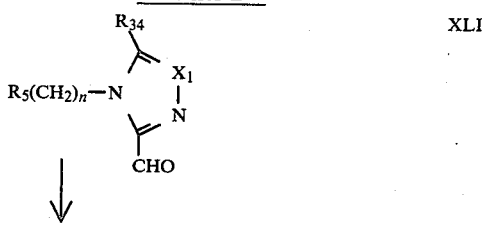
XLI -continued
CHART D
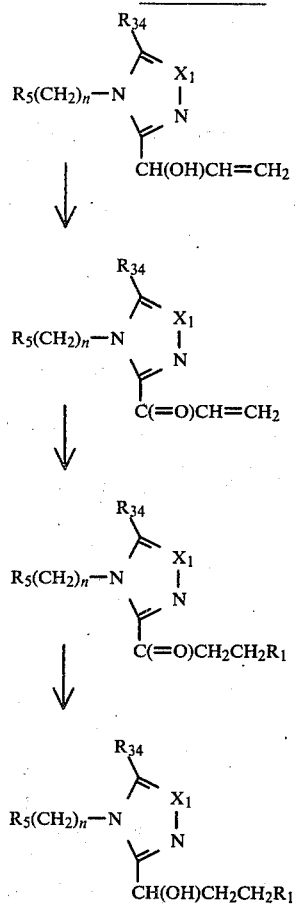
CHART E
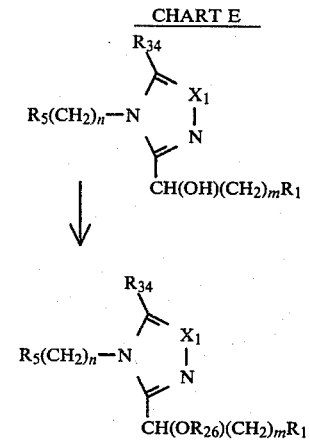
CHART F
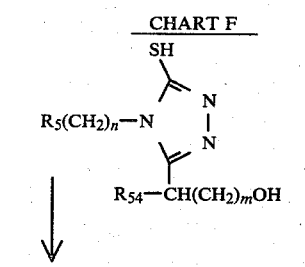
-continued
CHART F
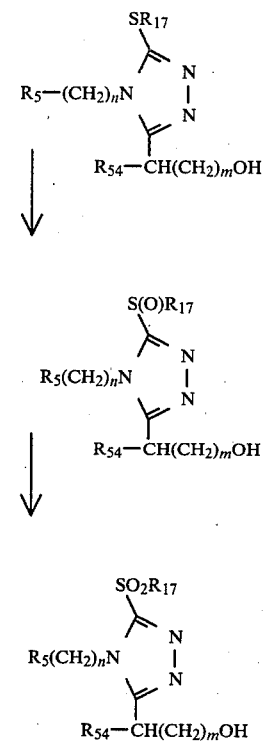
CHART G
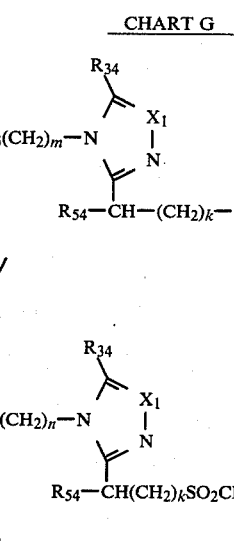
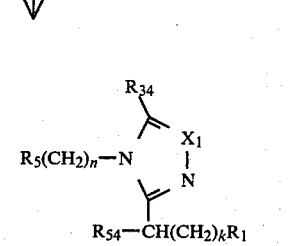

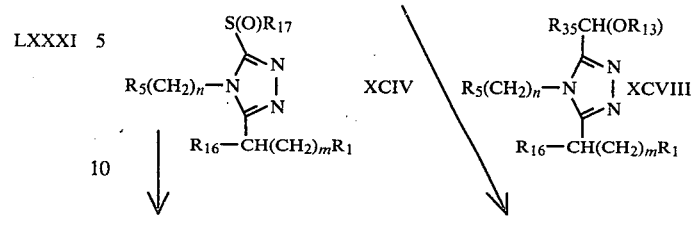
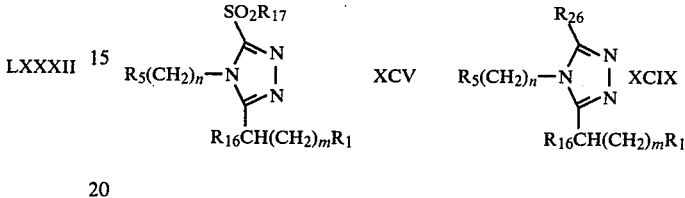
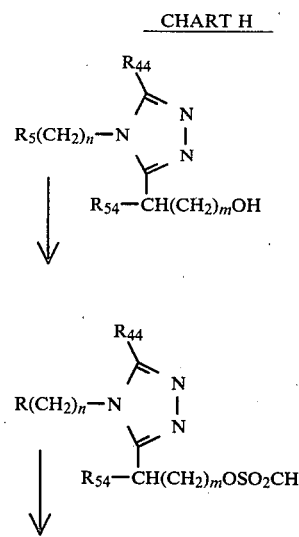
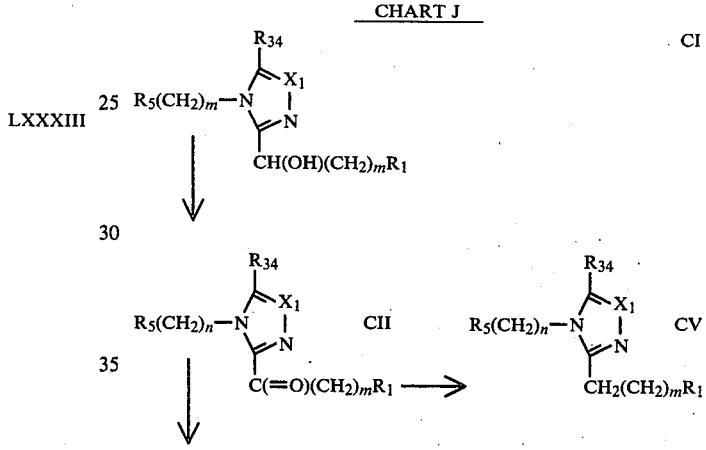
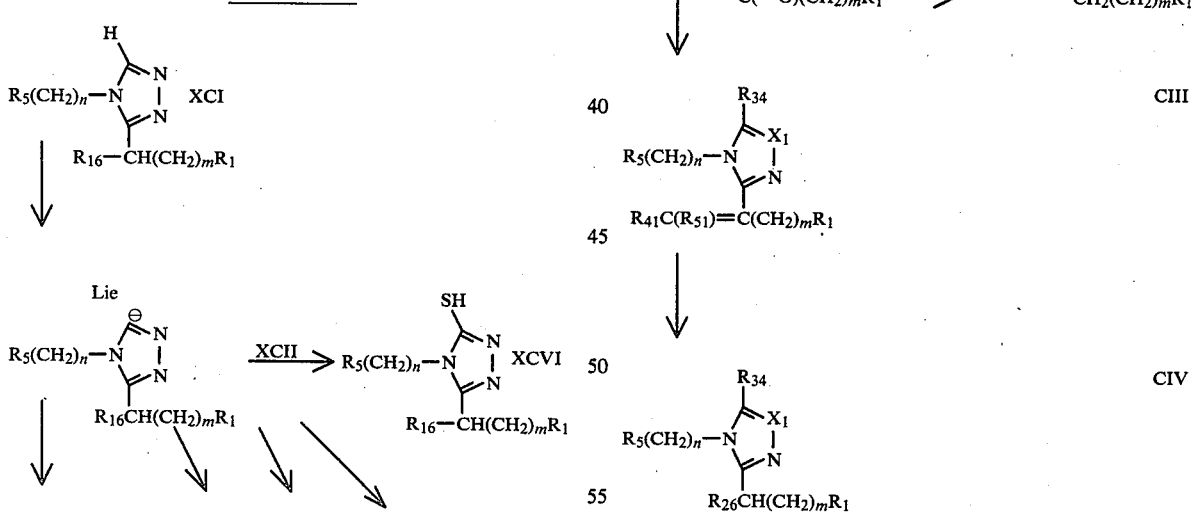
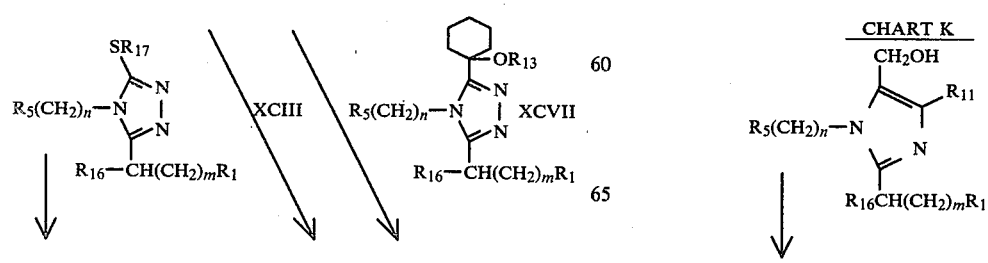
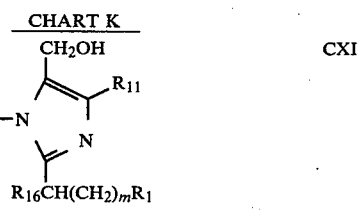

CHART K -continued

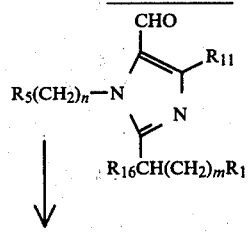

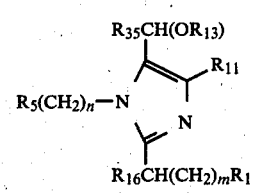

CHART L

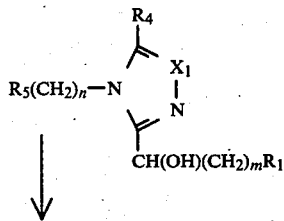

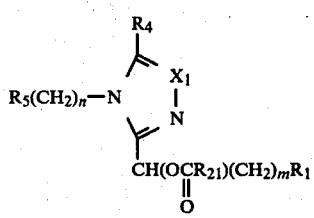

CHART M

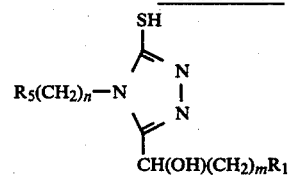

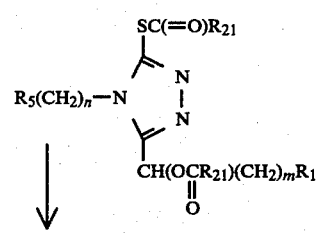

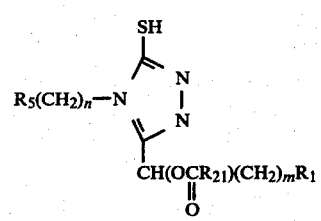

I claim:
1. A compound according to formula 1

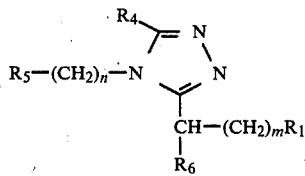

or a pharmacologically acceptable salt thereof,
wherein m is zero, one, 2 or 3;
wherein n is zero, one or 2,
wherein $R_1$ is:
  (a) 1-piperidinyl substituted at the 3 or 4 position by $R_{15}$, wherein $R_{15}$ is defined as below;
  (b) —N(CH$_3$)—(CH$_2$)$_p$—R$_{15}$, wherein $R_{15}$ and p are defined as below and wherein p is 1, 2, or 3; or
  (c) —NH—(CH$_2$)$_p$—R$_{15}$ wherein $R_{15}$ is as defined as below and wherein p is 1, 2, or 3;
wherein $R_4$ is:
  (a) hydrogen;
  (b) alkyl of one to three carbon atoms, inclusive;
  (c) $R_{54}OCH_2$—, wherein $R_{54}$ is as defined below;
  (d) —CH($R_{35}$)(OH);
  (e) —$R_{35}$
  (f) —SH;
  (g) $S(O)_qR_{17}$, wherein q is zero, one or two; and $R_{17}$ is as defined below;
  (h) 1-hydroxy-1-cyclohexyl; or
  (i) 1-cyclohexen-1yl;
wherein $R_5$, $R_{15}$, $R_{25}$, and $R_{35}$ are the same or different and are
  (i) 2, 3, or 4 pyridinyl, or
  (ii) phenyl substituted by zero to 2 chloro, fluoro, bromo, alkyl of from one to 3 carbon atoms, or alkoxy of from one to 3 carbon atoms, or
  (iii) phenyl substituted by one trifluoromethyl and zero to one of the previous phenyl substituents;
wherein $R_6$ is:
  (a) hydrogen;
  (b) —OR$_{54}$;
  (c) alkanoyloxy of from one to 3 carbon atoms; or
  (d) alkyl of from one to 3 carbon atoms; with the proviso that when m is zero, $R_6$ does not contain oxygen; and
wherein $R_{17}$ is methyl, phenyl, benzyl, or 2-phenylethyl; and wherein $R_{54}$ is hydrogen or alkyl of one to 3 carbon atoms; or an enantiomer when $R_4$ is —CH($R_{35}$)OH or when $R_6$ is not hydrogen or diastereomer when $R_4$ is —CH($R_{35}$)OH and $R_6$ is not hydrogen of such compound.

2. A compound of claim 1, wherein n is zero and $R_6$ is hydrogen.

3. A compound of claim 2, wherein m is 2.

4. A compound of claim 1 selected from the group consisting of
N-methyl-4-phenyl-N-(2-phenylethyl)-4H-1,2,4-triazole-3-propanamine,
5-methyl-4-phenyl-N-(2-phenylethyl)-4H-1,2,4-triazole-3-ethaneamine,
N,5-dimethyl-4-phenyl-N-(2-phenylethyl)-4H-1,2,4-triazole-3-ethaneamine, N-[2-(4-chlorophenyl)-ethyl]-N-methyl-4-phenyl-4H-1,2,4-triazole-3-propanamine,
4-(Phenylmethyl)-2-[3-(4-phenyl-4H-1,2,4-triazol-3-yl(propyl]-piperidine,
N-[2-(3,4-dichlorophenyl)-ethyl]-N-methyl-4-phenyl-4H-1,2,4-triazol-3-propanamine,
α-[[[2-(3,4-dichlorophenyl(ethyl]methylamino]methyl]-5-methyl-4-phenyl-4H-1,2,4-triazole-3-methanol,
α-[[[2-(4-chlorophenyl)ethyl]methylamino]methyl]-5-methyl-4-phenyl-4H-1,2,4-triazol-3-methanol, and
5-[3-[methyl(phenylethyl)amino]propyl]-α-4-diphenyl-4H-1,2,4-triazol-3-methanol.

5. N-methyl-4-phenyl-N-(2-phenylethyl)-4H-1,2,4-triazole-3-propanamine, a compound of claim 4.

6. A compound of claim 2, wherein m is one or two, and $R_4$ is hydrogen, methyl, hydroxymethyl, $S(O)_qR_{17}$ wherein q is zero, or —$CH(R_{35})$—(OH), wherein $R_5$ and $R_{35}$ are phenyl substituted by zero to 2 chloro, fluoro or bromo.

7. 5-Methyl-4-phenyl-N-(2-phenylethyl)-4H-1,2,4-triazole-3-ethanamine, a compound of claim 4.

8. N,5-Dimethyl-4-phenyl-N-(2-phenylethyl)-4H-1,2,4-triazole-3-ethaneamine, a compound of claim 4.

9. N-[2-(4-chlorophenyl)-ethyl]-N-methyl-4-phenyl-4H-1,2,4-triazole-3-propanamine, a compound of claim 4.

10. 4-(Phenylmethyl)-1-[3-(4-phenyl-4H-1,2,4-triazol-3-yl)-propyl]-piperidine, a compound of claim 4.

11. N-[2-(3,4-Dichlorophenyl)-ethyl]-N-methyl-4phenyl-4H-1,2,4-triazol-3-propanamine, a compound of claim 4.

12. α-[[[2-(3,4-Dichlorophenyl)ethyl]methylamino]-methyl]-5-methyl-4-phenyl-4H-1,2,4-triazole-3-methanol, a compound of claim 4.

13. α-[[4-(4-Chlorophenyl)-1-piperazinyl]methyl]-5-methyl-4-phenyl-4-1,2,4-triazole-3-methanol, a compound of claim 4.

14. α-[[[2-(4-Chlorophenyl)ethyl]methylamino]methyl]-5-methyl-4-phenyl-4H-1,2,4-triazol-3-methanol, a compound of claim 4.

15. 5-[3-[Methyl(phenylethyl)amino]propyl]-α-4-diphenyl-4H-1,2,4-triazol-3-methanol, a compound of claim 4.

16. 4-Phenyl-N-(2-phenylethyl)-4H-1,2,4-triazol-3-propan-amine, a compound of claim 4.

* * * * *